United States Patent [19]

Kawamoto et al.

[11] Patent Number: 4,894,385
[45] Date of Patent: Jan. 16, 1990

[54] IMIDAZOLE DERIVATIVES AS INHIBITORS OF TXA$_2$ SYNTHESIS

[75] Inventors: Isao Kawamoto; Rokuro Endo; Keiichi Matsuda; Shigeru Ushiyama; Takeshi Oshima, all of Tokyo, Japan

[73] Assignee: Sankyo Company Limited, Tokyo, Japan

[21] Appl. No.: 818,873

[22] Filed: Jan. 14, 1986

[30] Foreign Application Priority Data

Jan. 16, 1985 [JP] Japan ................................. 60-4055

[51] Int. Cl.$^4$ ................. A61K 31/415; C07D 405/06; C07D 409/06
[52] U.S. Cl. ................. 514/397; 514/227.8; 514/235.8; 514/252; 514/256; 514/318; 514/326; 514/333; 514/340; 514/341; 514/365; 514/383; 514/399; 544/58.5; 544/58.6; 544/58.7; 544/120; 544/122; 544/131; 544/132; 544/133; 544/139; 544/295; 544/296; 544/333; 544/357; 544/364; 544/369; 544/370; 544/405; 546/194; 546/209; 546/210; 546/256; 546/276; 546/278; 548/146; 548/204; 548/262; 548/336; 548/341
[58] Field of Search ............. 548/341; 514/399; 544/58.5, 58.6, 58.7, 120, 122, 131, 132, 133, 139, 295, 296, 333, 405, 357, 364, 369, 370; 546/194, 209, 210, 256, 276, 278

[56] References Cited

U.S. PATENT DOCUMENTS 4,632,934 12/1986 Iizuka et al. ..................... 514/399

FOREIGN PATENT DOCUMENTS 2031408 4/1980 United Kingdom ............ 544/341
2038821 7/1980 United Kingdom ............ 544/341

*Primary Examiner*—Richard A. Schwartz
*Attorney, Agent, or Firm*—Frishauf, Holtz Goodman & Woodward

[57] ABSTRACT

Compounds of formula (I):

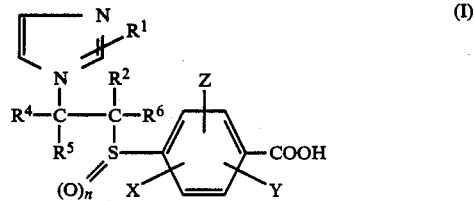

(wherein n is 0, 1 or 2 and $R^1$, $R^2$, $R^4$, $R^5$, $R^6$, X, Y and Z are a variety of groups and atoms) have the ability to inhibit the synthesis of thromboxane A$_2$ and hence are useful in the treatment or prophylaxis of thrombotic conditions.

34 Claims, No Drawings

IMIDAZOLE DERIVATIVES AS INHIBITORS OF TXA₂ SYNTHESIS

The present invention relates to a series of new imidazole derivatives which are useful in the treatment of disorders arising from an imbalance in the metabolic levels of the prostaglandin derivative, thromboxane A$_2$ (hereinafter simply referred to as "TXA$_2$"). The invention also provides processes for producing such imidazole derivatives.

Many of the compounds within the group known generally as "prostaglandins" are known to have extremely important effects on the metabolism and functioning of the animal, including human, body, although, in most cases, the mode and often precise effect (or effects) of the individual compounds have not yet been elucidated. It is known that TXA$_2$ has a fundamental role in inducing platelet aggregation and constricting the smooth muscles of the arteries and it is known that this compound is produced from prostaglandin endoperoxide PGH$_2$ via PGG$_2$. It is known that the activity of TXA$_2$ is generally opposite to that of PGI$_2$, which causes vasodilation and prevents platelet aggregation. Accordingly, it has been suggested that the balance within the blood between TXA$_2$ and PGI$_2$ is a controlling factor in the development and/or cure of thrombosis. Accordingly, it is desirable for the treatment or prophylaxis of thromboembolisms to inhibit selectively the synthesis of TXA$_2$ and thereby to enhance the activity of PGI$_2$, which has an inhibitory effect on platelet aggregation, and also to increase the level of PGI$_2$ as a result of accumulation of PGH$_2$. It is believed that an effective inhibitor of the synthesis of TXA$_2$ would be of considerable value in the treatment or prophylaxis of a variety of diseases and disorders associated with the circulatory system. It is, however, important that this inhibitory activity should not be accompanied by inhibition of the enzymes responsible for the synthesis of other prostaglandins.

Needleman et al have shown [Prostaglandins, 13, 611 (1977)] that imidazole and 1-methylimidazole have some inhibitory effect on the synthesis of TXA$_2$. However, the inhibitory activity is insufficient for the compounds to be of practical use. Subsequently, certain other imidazole derivatives were discovered and have been proposed for therapeutic use in the treatment or prophylaxis of diseases and disorders caused by an imbalance in the level of TXA$_2$ (see, for example, GB Patent Specifications No. 2,038,821 and No. 2,031,408).

We have now discovered a series of novel imidazole derivatives which have a very powerful inhibitory effect on the synthesis of TXA$_2$ and thus have a very pronounced therapeutic activity. The activities of the compounds of the invention are significantly (in some cases by an order of magnitude) better than those of the prior art compounds.

BRIEF SUMMARY OF INVENTION

The compounds of the present invention are those compounds of formula (I):

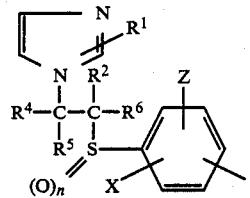

wherein:
R$^1$ represents a hydrogen atom or a methyl group;
R$^2$ represents a hydrogen atom, a C$_1$–C$_6$ alkyl group, a C$_2$–C$_6$ alkenyl group, a C$_2$–C$_6$ alkynyl group, a C$_3$–C$_8$ cycloalkyl group, an aryl group, a heterocyclic group or a carboxy group, or one of said alkyl, alkenyl and alkynyl groups having at least one substituent selected from the group consisting of:
(a) C$_1$–C$_4$ alkoxy groups, carboxylic acyloxy groups, carboxylic acyl groups, carboxy groups, C$_2$–C$_7$ alkoxycarbonyl groups, C$_2$–C$_7$ alkoxycarbonyloxy groups, carbamoyloxy groups, alkylcarbamoyloxy groups in which the alkyl part is C$_1$–C$_4$ alkyl, dialkylcarbamoyloxy groups in which each alkyl part is C$_1$–C$_4$ alkyl, carbamoyl groups, alkylcarbamoyl groups in which the alkyl part is C$_1$–C$_4$ alkyl, dialkylcarbamoyl groups in which each alkyl part is C$_1$–C$_4$ alkyl, hydroxy groups, carboxylic acylamino groups, C$_1$–C$_6$ alkylthio groups, nitro groups, cyano groups, amino groups, C$_1$–C$_6$ haloalkyl groups, C$_1$–C$_6$ alkylsulfinyl groups, C$_1$–C$_6$ alkylsulfonyl groups, C$_3$–C$_8$ cycloalkyl groups, C$_3$–C$_8$ cycloalkyl groups having at least one substituent selected from the group consisting of substituents (a) and (b), aryl groups and heterocyclic groups,
or a C$_3$–C$_8$ cycloalkyl group having at least one substituent selected from the group consisting of substituents (a) and substituents (b):
(b) C$_1$–C$_6$ alkyl groups;
R$^4$ represents a hydrogen atom, a C$_1$–C$_6$ alkyl group, a C$_2$–C$_6$ alkenyl group, a C$_2$–C$_6$ alkynyl group, an aryl group or an aromatic heterocyclic group, or said alkyl, alkenyl or alkynyl group having at least one substituent selected from the group consisting of:
(c) C$_1$–C$_6$ alkoxy groups, C$_1$–C$_6$ haloalkyl groups, halogen atoms, aryl groups and aromatic heterocyclic groups;
R$^5$ and R$^6$ are independently selected from the group consisting of hydrogen atoms, C$_1$–C$_6$ alkyl groups, C$_2$–C$_6$ alkenyl groups and C$_2$–C$_6$ alkynyl groups;
X, Y and Z are independently selected from the group consisting of hydrogen atoms, C$_1$–C$_6$ alkyl groups, C$_1$–C$_6$ alkoxy groups, C$_1$–C$_6$ alkanoyloxy groups, hydroxy groups, C$_1$–C$_6$ alkylthio groups, cyano groups, amino groups, halogen atoms, C$_1$–C$_6$ alkylsulfinyl groups and C$_1$–C$_6$ alkylsulfonyl groups;
n is 0, 1 or 2;
said aryl groups are C$_6$–C$_{14}$ carbocyclic aryl groups which are unsubstituted or have at least one substituent selected from the group consisting of substituents (a) other than said aryl groups and (b); and
said heterocyclic groups have from 5 to 14 ring atoms of which from 1 to 5 are hetero-atoms selected from the group consisting of nitrogen, oxygen and sulfur atoms, said hetrocyclic groups being unsubstituted or having at least one substituent selected from the group consisting of substituents (a) other than said heterocyclic groups and (b);

provided that $R^2$, $R^4$, and $R^5$ and $R^6$ do not simultaneously represent hydrogen atoms;

and pharmaceutically acceptable esters, amides and salts thereof.

In particular, we prefer that $R^2$, $R^4$, $R^5$ and $R^6$ should not simultaneously be selected from the group consisting of hydrogen atoms and unsubstituted alkyl, alkenyl and possibly alkynyl groups.

The invention further provides a pharmaceutical composition comprising an active compound in admixture with a pharmaceutically acceptable carrier or diluent, wherein the active compound is selected from the group consisting of compounds of formula (I) and pharmaceutically acceptable esters, amides and salts thereof.

The invention still further provides a method for the treatment of prophylaxis of diseases and disorders arising from an imbalance in the level of $TXA_2$ in an animal, normally mammal, including human being, which comprises administering to said animal an effective amount of an inhibitor of the synthesis of $TXA_2$, wherein said inhibitor is selected from the group consisting of compounds of formula (I) and pharmaceutically acceptable esters, amides and salts thereof.

DETAILED DESCRIPTION OF INVENTION

In the compounds of the invention where $R^2$, $R^4$, $R^5$, $R^6$, X, Y, Z or substituent (b) represents a $C_1$–$C_6$ alkyl group, this may be a straight or branched chain alkyl group and examples include the methyl, ethyl, propyl, isopropyl, butyl, isobutyl, sec-butyl, t-butyl, pentyl, isopentyl, neopentyl, hexyl and isohexyl groups.

Where $R^2$, $R^4$, $R^5$ or $R^6$ represents a $C_2$–$C_6$ alkenyl group, this may be a straight or branched chain group and is more preferably a $C_2$–$C_4$ alkenyl group, for example a vinyl, allyl, isopropenyl or 2-butenyl group.

Where $R^2$, $R^4$, $R^5$ or $R^6$ represents a $C_2$–$C_6$ alkynyl group, this may be a straight or branched chain group and is preferably a $C_2$–$C_4$ alkynyl group, for example an ethynyl, 2-propynyl or 2-butynyl group.

Where $R^2$ or said substituent (a) represents a cycloalkyl group, this has from 3 to 8, preferably from 3 to 6, ring carbon atoms and examples include the cyclopropyl, cyclobutyl, cyclopentyl and cyclohexyl groups.

Where $R^2$, $R^4$, substituent (a) or substituent (c) represents an aryl group, this is a carbocyclic aryl group having from 6 to 14, preferably from 6 to 10 ring atoms and may be a monocyclic or fused polycyclic ring system, preferably a phenyl, α-naphthyl or β-naphthyl group. Such a group may be unsubstituted or may have at least one substituent selected from the groups defined above as substituents (a) (other than said aryl groups) and (b).

Where $R^2$ or substituent (a) is a heterocyclic group, this may be an aromatic or non-aromatic (including fully or partially saturated) heterocyclic group having from 5 to 14, more preferably from 5 to 8 and most preferably 5 or 6, ring atoms, of which from 1 to 5, preferably from 1 to 3 and more preferably 1 or 2, are hetero-atoms selected from the group consisting of nitrogen, oxygen and sulfur atoms. Such groups may be unsubstituted or may have at least one substituent selected from the groups defined above as substituents (a) (other than said heterocyclic groups) and (b). Examples of such aromatic heterocyclic groups include the 2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl groups. Examples of such non-aromatic heterocyclic groups include the 2-tetrahydrofuryl, 2-tetrahydropyranyl, 2-pyrrolidinyl, 1-pyrrolidinyl, piperidino, 2-piperidyl, 3-piperidyl, 4-piperidyl, 4-thiazolidinyl, 1-piperazinyl, 4-acetyl-1-piperazinyl, 4-formyl-1-piperazinyl, morpholino and thiomorpholino groups.

Where $R^4$ or substituent (c) represents an aromatic heterocyclic group this is as defined above in relation to $R^2$ and examples include those aromatic heterocycles exemplified above.

Where X, Y, Z or substituent (a) or (c) represents a $C_1$–$C_6$ alkoxy group, this may be a straight or branched chain group and is preferably a $C_1$–$C_4$ group. Examples of such groups include the methoxy, ethoxy, propoxy, isopropoxy, butoxy and isobutoxy groups.

Where X, Y or Z represents a $C_1$–$C_6$ alkanoyloxy group, this likewise may be a straight or branched chain group and is preferably a $C_2$–$C_4$ alkanoyloxy group, for example an acetoxy, propionyloxy, butyryloxy or isobutyryloxy group.

Where X, Y, Z or substituent (a) represents a $C_1$–$C_6$ alkylthio group, this may be a straight or branched chain group and is preferably such a group having from 1 to 4 carbon atoms. Examples of such groups include the methylthio, ethylthio, propylthio, isopropylthio, butylthio and isobutylthio groups.

Where X, Y, Z or substituent (a) or (c) represents a halogen atom, this is preferably a fluorine, chlorine or bromine atom.

Where X, Y, Z or substituent (a) represents a $C_1$–$C_6$ alkylsulfinyl group or a $C_1$–$C_6$ alkylsulfonyl group, each alkyl part is preferably a $C_1$–$C_6$ alkyl group, such as those exemplified above in relation to $R^2$, more preferablly a $C_1$–$C_4$ an most preferably a $C_1$–$C_2$, group, and examples of such alkylsulfinyl and alkylsulfonyl groups include the methanesulfinyl, methanesulfonyl, ethanesulfinyl, ethanesulfonyl, propanesulfinyl and propanesulfonyl groups.

Where substituent (a) represents an acyloxy group, this is preferably a $C_1$–$C_6$ alkanoyloxy group, e.g. those exemplified above in relation to X, Y and Z, or an arylcarbonyl group, in which the aryl part is preferably as defined above in relation to the aryl groups which may be represented by $R^2$. Specific examples of such acyloxy groups include the acetoxy, propionyloxy, butyryloxy, isobutyryloxy, benzoyloxy, p-toluoyloxy, p-anisoyloxy and p-chlorobenzoyloxy groups.

Where substituent (a) is a carboxylic acyl group, this is preferably an alkanoyl group having from 1 to 6, preferably from 1 to 4, carbon atoms, for example a formyl, acetyl, propionyl, butyryl or isobutyryl group.

Where substituent (a) represents an alkoxycarbonyl or alkoxycarbonyloxy group, these are preferably $C_2$–$C_7$ groups (i.e. the alkoxy part is $C_1$–$C_6$), more preferably $C_2$–$C_5$ groups, for example the methoxycarbonyl, ethoxycarbonyl, propoxycarbonyl, butoxycarbonyl, isobutoxycarbonyl, methoxycarbonyloxy, ethoxycarbonyloxy, propoxycarbonyloxy, butoxycarbonyloxy and isobutoxycarbonyloxy groups.

Where substituent (a) represents a mono- or di-alkylcarbamoyl group or a mono- or di-alkylcarbamoyloxy group, the alkyl parts are $C_1$–$C_4$ alkyl groups, preferably selected amongst those alkyl groups listed above in relation to $R^2$, and, in the case of the di-substituted groups, the two alkyl groups may be the same or different. Specific examples of such groups include the methylcarbamoyl, ethylcarbamoyl, propylcarbamoyl, isopropylcarbamoyl, butylcarbamoyl, isobutylcarbamoyl, dimethylcarbamoyl, diethylcarbamoyl, dipropylcarbamoyl, diisopropylcarbamoyl, dibutylcarbamoyl, methylcarbamoyloxy, ethylcarbamoyloxy, propylcarbamoyloxy, isopropylcarbamoyloxy, butylcarbamoyloxy, isobutylcarbamoyloxy, dimethylcarbamoyloxy, diethylcarbamoyloxy, dipropylcarbamoyloxy, diisopropylcarbamoyloxy and dibutylcarbamoyloxy groups.

Where substituent (a) represents an acylamino group, the acyl part may be as defined above in relation to acyl groups and examples of such acylamino groups include the acetamido, propionamido and benzamido groups.

Where substituent (a) or (c) represents a haloalkyl group, this is a straight or branched chain group containing from 1 to 6 carbon atoms and at least one halogen atom, which may be a fluorine, chlorine, bromine or iodine atom but is preferably a fluorine atom. More preferably, the haloalkyl group is a $C_1$–$C_3$, most preferably $C_1$, group and the number of halogen atoms may range from a single halogen atom to perhalogenation. Examples of such haloalkyl groups include the fluoromethyl, chloromethyl, bromomethyl, trifluoromethyl, 2-chloroethyl, 2-fluoroethyl, 2,2-dichloroethyl, 2,2,2-trichloroethyl, 3-chloropropyl and 2,3-dichloropropyl groups.

Where $R^2$ or $R^4$ represents an alkyl group having an aryl substituent, i.e. an aralkyl group, the aryl part is preferably as defined above in relation to the aryl groups which may be represented by $R^2$, whilst the alkyl group is most preferably a $C_1$–$C_3$ alkyl group and examples of such aralkyl groups thus include the benzyl, phenethyl, α-methylbenzyl, 3-phenylpropyl, α-naphthylmethyl, 2-(α-naphthyl)ethyl and 2-(62-naphthyl)ethyl groups.

Where $R^2$ or $R^4$ represents an alkenyl or alkynyl group having an aryl substituent, i.e. an aralkenyl or aralkynyl group, the aryl part is preferably as defined above in relation to the aryl groups which may be represented by $R^2$ and the alkenyl or alkynyl part is preferably a $C_2$–$C_3$ alkenyl or alkynyl group, for example a cinnamoyl or 2-phenylethynyl group.

Where $R^2$ represents an alkyl group having a cycloalkyl substituent, the cycloalkyl part is preferably as defined above in relation to the cycloalkyl groups which may be represented by $R^2$ and is more preferably a $C_3$–$C_6$ cycloalkyl group, whilst the alkyl part is preferably a $C_1$–$C_3$ alkyl group. Examples of such groups include the cyclopropylmethyl, cyclobutylmethyl, cyclopentylmethyl, 2-cyclopentylethyl, 3-cyclopentylpropyl, cyclohexylmethyl, 2-cyclohexylethyl and 3-cyclohexylpropyl groups.

Where $R^2$ or $R^4$ represents an alkyl group having a heterocyclic substituent, the heterocyclic part is preferably as defined above in relation to $R^2$ or $R^4$, respectively, whilst the alkyl part is preferably a $C_1$–$C_3$, more preferably $C_1$ or $C_2$, alkyl group. Examples of aromatic heterocyclic-alkyl groups which may be represented by $R^2$ or $R^4$ include the furfuryl, 2-thenyl, 3-thenyl, 1-imidazolylmethyl, 1,2,4-triazol-1-ylmethyl, 2-pyridylmethyl, 2-pyrimidylmethyl, 2-furylethyl, 2-(2- or 3-thienyl)ethyl, 2-(2-pyridyl)ethyl, 2-(3-pyridyl)ethyl, 2-(4-pyridyl)ethyl and 2-(2-thiazolyl)ethyl groups. Examples of non-aromatic heterocyclic-alkyl groups which may be represented by $R^2$ include the 2-(2-tetrahydrofuryl)ethyl, 2-(2-tetrahydropyranyl)ethyl, 1-pyrrolidinylmethyl, piperidinomethyl, piperazinylmethyl, 4-acetyl-1-piperazinylmethyl, 4-formyl-1-piperazinylmethyl, morpholinomethyl, 2-morpholinoethyl and thiomorpholinomethyl groups.

Where any of the groups referred to above are substituted, there is, in principle, no restriction in accordance with the present invention as to the number of substituents which may be possible. Accordingly, the present invention, in referring to substituted groups, envisages such groups containing anything from a single substituent to complete substitution of all substitutable positions. However, in practice, as is well-known in the art, there may be practical limitations as to the number of possible substituents, arising from steric constraints. For example, where the substituent is relatively "small", for example a halogen atom, complete substitution (i.e. perhalogenation) may be possible. On the other hand, if the substituent is relatively "bulky" and the group to be substituted is relatively small, then steric constraints may limit the number of substituents, possibly even to a single substituent only. These factors are, however, well-known to all chemists. In general, where substituents are referred to, we would normally first consider from 1 to 3 such substituents, but it will be appreciated that, given the constraints described above, more substituents may be possible.

Preferred classes of compound of the present invention are as follows:

(1) Compounds of formula (I) in which:
$R^1$ represents a hydrogen atom or a methyl group;
$R^2$ represents a hydrogen atom, a $C_1$–$C_6$ alkyl group, a $C_2$–$C_6$ alkenyl group, a $C_2$–$C_6$ alkynyl group, a $C_3$–$C_6$ cycloalkyl group, an aryl group or an aromatic heterocyclic group, any of said groups being unsubstituted or having at least one substituent selected from the group consisting of substituents (a'):

(a') $C_1$–$C_6$ alkoxy groups, carboxylic acyloxy groups, hydroxy groups, $C_1$–$C_6$ alkylthio groups, cyano groups, trifluoromethyl groups, halogen atoms, $C_1$–$C_6$ alkylsulfinyl groups, $C_1$–$C_6$ alkylsulfonyl groups, aryl groups and aromatic heterocyclic groups, or said cycloalkyl group having at least one substituent selected from the group consisting of substituents (b), as defined above;

$R^4$ represents a hydrogen atom, a $C_1$–$C_6$ alkyl group, a $C_2$–$C_6$ alkenyl group, a $C_2$–$C_6$ alkynyl group, an aryl group or an aromatic heterocyclic group, any of said groups being unsubstituted or having at least one substituent selected from the group consisting of substituents (c'):

(c') $C_1$–$C_6$ alkoxy groups, trifluoromethyl groups and halogen atoms;

$R^5$ and $R^6$ are the same or different and each represents a hydrogen atom, a $C_1$–$C_6$ alkyl group, a $C_2$–$C_6$ alkenyl group or a $C_2$–$C_6$ alkynyl group;

X, Y and Z are the same or different and each represents a hydrogen atom, a $C_1$–$C_6$ alkyl group, a $C_1$–$C_6$ alkoxy group, a $C_1$–$C_6$ alkanoyloxy group, a hydroxy group, a $C_1$–$C_6$ alkylthio group, a cyano group, an amino group, a halogen atom, a $C_1$–$C_6$ alkylsulfinyl group, or a $C_1$–$C_6$ alkylsulfonyl group; and n is 0, 1 or 2;

said aryl groups being as defined above, but, where substituted, the substituents being selected from the group consisting of substituents (a') other than said aryl groups and (b);

said heterocyclic groups being as defined above, but, where substituted, the substituents being selected from the group consisting of substituents (a') other than said heterocyclic groups and (b);

(2) Compounds of formula (I) wherein:

$R^1$, $R^4$ and $R^5$ all represent hydrogen atoms;

$R^2$ represents a $C_3$-$C_6$ cycloalkyl group, an aryl group, an aralkyl group, an aromatic heterocyclic group or a $C_1$-$C_3$ alkyl group having an aromatic heterocyclic substituent, said groups being unsubstituted or having at least one substituent selected from the group consisting of substituents (a''):

(a'') $C_1$-$C_4$ alkyl groups, $C_1$-$C_4$ alkoxy groups, carboxylic acyloxy groups, hydroxy groups, trifluoromethyl groups and halogen atoms;

$R^6$ represents a hydrogen atom, a $C_1$-$C_4$ alkyl group, a $C_2$-$C_4$ alkenyl group or a $C_2$-$C_4$ alkynyl group;

X, Y and Z are independently selected from the group consisting of hydrogen atoms, $C_1$-$C_4$ alkyl groups and halogen atoms; and n is 0;

and pharmaceutically acceptable esters, amides and salts of said compounds.

The compounds of the invention necessarily contain at least one carboxy group at the 4-position of the benzene ring and may, where $R^2$ represents a carboxy group, also contain a second carboxy group. These two carboxy groups may, independently of each other, form esters, amides and salts and, where such esters, amides or salts are formed, the two groups may be the same of different.

Where $R^2$ represents an esterified carboxy group or the carboxy group on the benzene ring is esterified, the nature of the resulting ester is not critical to the present invention. In principle, the compounds of the invention, being carboxylic acids, will form esters with any ester-forming alcohol and all such esters form part of the present invention. However, where the esters are to be employed for therapeutic purposes, it is, of course, necessary that the resulting esters should be pharmaceutically acceptable, which as is understood in the art, means that the esters should not have reduced activity, or substantially reduced activity, and should not have increased toxicity, or substantially increased toxicity, as compared with the free acid. However, where the ester is to be employed for other purposes, for example as an intermediate in the preparation of other compounds, even this criterion does not apply.

Examples of such esters include $C_1$-$C_6$, and preferably $C_1$-$C_4$ alkyl esters, for example the methyl, ethyl, propyl, isopropyl, butyl, isobutyl, sec-butyl, t-butyl, pentyl and hexyl esters; aralkyl and diarylalkyl esters, such as the benzyl, p-nitrobenzyl and benzhydryl esters; alkoxycarbonylalkyl esters, in which the alkoxy and alkyl parts are both $C_1$-$C_4$, especially alkoxycarbonylmethyl esters, such as the ethoxycarbonylmethyl and t-butoxycarbonylmethyl esters; alkoxycarbonyloxyalkyl esters in which the alkoxy and alkyl parts are both $C_1$-$C_4$, especially 2-(alkoxycarbonyloxy)ethyl esters, such as the 2-methoxycarbonyloxyethyl, 2-ethoxycarbonyloxyethyl and 2-t-butoxycarbonyloxyethyl esters; and other specific esters, such as the phthalidyl, substituted phthalidyl and (5-methyl-2-oxo-1,3-dioxolen-4-yl)methyl esters.

Likewise, where either or both carboxy group has formed an amide, the precise nature of the amide is not critical, provided that, where the amide is to be used for therapeutic purposes, the resulting amide is pharmaceutically acceptable. Accordingly, either or both of these carboxy groups can be replaced by a carbamoyl group or a substituted carbamoyl group, preferably an alkylcarbamoyl or dialkylcarbamoyl group [e.g. as defined above in relation to substituents (a)], for example a methylcarbamoyl, ethylcarbamoyl, dimethylcarbamoyl or diethylcarbamoyl group.

Either or both of these carboxy groups may also form salts with appropriate bases. Additionally, since the imidazole nitrogen atoms are basic in character, the compounds of the invention also form acid addition salts. The nature of such salts is likewise not critical, provided that, where they are to be used for therapeutic purposes, the salts are pharmaceutically acceptable. A wide range of acids can form acid addition salts with the compounds of the invention and examples of such acids include: mineral acids, such as hydrochloric acid, hydrobromic acid, nitric acid and phosphoric acid; organic carboxylic acids, such as acetic acid, trifluoroacetic acid, asparaginic acid, glutamic acid, oxalic acid, tartaric acid, citric acid, maleic acid, fumaric acid, lactic acid, salicylic acid, malonic acid and succinic acid; and organic sulfonic acids, such as methanesulfonic acid, benzenesulfonic acid and p-toluenesulfonic acid.

Examples of salts with bases include: salts with metals, especially alkali metals and alkaline earth metals, such as the lithium, sodium, potassium, calcium and magnesium salts; ammonium salt; salts with organic amines, such as cyclohexylamine, diisopropylamine or triethylamine; and salts with basic amino acids, such as lysine or arginine.

The compounds of the invention contain at least one and may contain several asymmetric carbon atoms and, accordingly, optical isomers of the compounds are possible. Although the various optical isomers are all represented herein by a single formula, the present invention embraces both the individual isolated isomers and mixtures thereof.

Examples of specific compounds of the invention are given in the following Tables 1 to 3. The compounds of the invention are hereinafter, where appropriate, identified by the numbers appended to them in these Tables. In the Tables, the following abbreviations are used:

| | |
|---|---|
| Ac | acetyl |
| All | allyl |
| iBu | isobutyl |
| tBu | t-butyl |
| Bz | benzyl |
| Car | carbamoyl |
| cPr | cyclopropyl |
| cPn | cyclopentyl |
| cHx | cyclohexyl |
| Dox | (5-methyl-2-oxo-1,3-dioxolen-4-yl)methyl |
| Et | ethyl |
| Fur | furyl |
| Imid | imidazolyl |
| Me | methyl |
| Mor | morpholino |
| Ph | phenyl |
| Phth | phthalidyl |
| Pip | piperidyl |
| Piz | piperazinyl |
| Pr | propyl |
| iPr | isopropyl |
| Pym | pyrimidinyl |
| Prg | propargyl (= 2-propynyl) |
| Pyr | pyridyl |
| Pyrd | pyrrolidinyl |
| Pyrr | pyrrolyl |
| Pyz | pyrazinyl |

-continued

| | | |
|---|---|---|
| Thf | tetrahydrofuryl | |
| Thi | thienyl | |
| Thiz | 1,3-thiazolyl | |
| Thp | tetrahydropyranyl | |
| Thz | perhydro-1,4-thiazin-4-yl (= thiomorpholino) | |
| Triz | 2H—1,2,4-triazolyl | |

Compounds of formula (I-1):

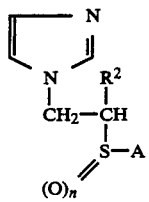

are as defined in Table 1:

TABLE 1

| Cpd No | R² | A | n |
|---|---|---|---|
| 1 | —CH₂F | 4-(HOCO)Ph | 0 |
| 2 | —CH₂OH | 4-(HOCO)Ph | 0 |
| 3 | —CH₂OCar | 4-(HOCO)Ph | 0 |
| 4 | —CH₂OAc | 4-(HOCO)Ph | 0 |
| 5 | —CH₂OCONMe₂ | 4-(HOCO)Ph | 0 |
| 6 | MeOCH₂— | 4-(HOCO)Ph | 0 |
| 7 | —CH₂OCOOEt | 4-(HOCO)Ph | 0 |
| 8 | —CH₂SMe | 4-(HOCO)Ph | 0 |
| 9 | —CH₂CN | 4-(HOCO)Ph | 0 |
| 10 | —CH₂NH₂ | 4-(HOCO)Ph | 0 |
| 11 | —CH₂NHAc | 4-(HOCO)Ph | 0 |
| 12 | —CH₂COOH | 4-(HOCO)Ph | 0 |
| 13 | —CH₂Car | 4-(HOCO)Ph | 0 |
| 14 | —CH₂OCONHMe | 4-(HOCO)Ph | 0 |
| 15 | —CH₂OCar | 4-(HOCO)Ph | 0 |
| 16 | 2-OHEt | 4-(HOCO)Ph | 0 |
| 17 | 3-OHPr | 4-(HOCO)Ph | 0 |
| 18 | 2-(CarO)Et | 4-(HOCO)Ph | 0 |
| 19 | 3-(CarO)Pr | 4-(HOCO)Ph | 0 |
| 20 | 2-CN—Et | 4-(HOCO)Ph | 0 |
| 21 | 2-(MeOCO)Et | 4-(HOCO)Ph | 0 |
| 22 | 2-(HOCO)Et | 4-(HOCO)Ph | 0 |
| 23 | 2-(tBuOCO)Et | 4-(HOCO)Ph | 0 |
| 24 | 2-CarEt | 4-(HOCO)Ph | 0 |
| 25 | 2-(EtOCO)Et | 4-(HOCO)Ph | 0 |
| 26 | —CH=CH—COOH | 4-(HOCO)Ph | 0 |
| 27 | —CH=CH—COOEt | 4-(HOCO)Ph | 0 |
| 28 | cPr | 4-(HOCO)Ph | 0 |
| 29 | cPn | 4-(HOCO)Ph | 0 |
| 30 | cHx | 4-(HOCO)Ph | 0 |
| 31 | cHx | 4-(MeOCO)Ph | 0 |
| 32 | —CH₂—cPr | 4-(HOCO)Ph | 0 |
| 33 | 2-cPrEt | 4-(HOCO)Ph | 0 |
| 34 | —CH₂—cPn | 4-(HOCO)Ph | 0 |
| 35 | —CH₂—cHx | 4-(HOCO)Ph | 0 |
| 36 | 2-cHxEt | 4-(HOCO)Ph | 0 |
| 37 | 2-cPnEt | 4-(HOCO)Ph | 0 |
| 38 | Ph | 4-(MeOCO)Ph | 0 |
| 39 | Ph | 4-(EtOCO)Ph | 0 |
| 40 | Ph | 4-(HOCO)Ph | 0 |
| 41 | 4-FPh | 4-(MeOCO)Ph | 0 |
| 42 | 4-FPh | 4-(HOCO)Ph | 0 |
| 43 | 2,4-diClPh | 4-(MeOCO)Ph | 0 |
| 44 | 2,4-diClPh | 4-(HOCO)Ph | 0 |
| 45 | 2-BrPh | 4-(HOCO)Ph | 0 |
| 46 | 4-BrPh | 4-(HOCO)Ph | 0 |
| 47 | 3-ClPh | 4-(HOCO)Ph | 0 |
| 48 | 4-ClPh | 4-(HOCO)Ph | 0 |
| 49 | 2-ClPh | 4-(HOCO)Ph | 0 |
| 50 | 2-ClPh | 4-(MeOCO)Ph | 0 |
| 51 | 2-FPh | 4-(HOCO)Ph | 0 |
| 52 | 3-FPh | 4-(HOCO)Ph | 0 |
| 53 | 2,6-diClPh | 4-(HOCO)Ph | 0 |
| 54 | 2,4-diFPh | 4-(HOCO)Ph | 0 |
| 55 | 2,6-diFPh | 4-(HOCO)Ph | 0 |
| 56 | 2,5-diFPh | 4-(HOCO)Ph | 0 |
| 57 | 4-MePh | 4-(HOCO)Ph | 0 |
| 58 | 2-MePh | 4-(HOCO)Ph | 0 |
| 59 | 4-MePh | 4-(MeOCO)Ph | 0 |
| 60 | 2-MePh | 4-(MeOCO)Ph | 0 |
| 61 | 3,4-diMePh | 4-(HOCO)Ph | 0 |
| 62 | 2,4,6-triMePh | 4-(HOCO)Ph | 0 |
| 63 | 2,4,6-triMePh | 4-(MeOCO)Ph | 0 |
| 64 | 2,6-diMePh | 4-(HOCO)Ph | 0 |
| 65 | 3-CF₃Ph | 4-(HOCO)Ph | 0 |
| 66 | 2-CF₃Ph | 4-(HOCO)Ph | 0 |
| 67 | 2-CF₃Ph | 4-(MeOCO)Ph | 0 |
| 68 | 4-CF₃Ph | 4-(MeOCO)Ph | 0 |
| 69 | 4-CF₃Ph | 4-(HOCO)Ph | 0 |
| 70 | 2-MeOPh | 4-(HOCO)Ph | 0 |
| 71 | 3-MeOPh | 4-(HOCO)Ph | 0 |
| 72 | 3-MeOPh | 4-(MeOCO)Ph | 0 |
| 73 | 4-MeOPh | 4-(HOCO)Ph | 0 |
| 74 | 2,4-diMeOPh | 4-(HOCO)Ph | 0 |
| 75 | 2,4-diMeOPh | 4-(MeOCO)Ph | 0 |
| 76 | 2,5-diMeOPh | 4-(HOCO)Ph | 0 |
| 77 | 3,4-diMeOPh | 4-(HOCO)Ph | 0 |
| 78 | 3,5-diMeOPh | 4-(HOCO)Ph | 0 |
| 79 | 2,6-diMeOPh | 4-(HOCO)Ph | 0 |
| 80 | 2,6-diMeOPh | 4-(MeOCO)Ph | 0 |
| 81 | 2,3,4-triMeOPh | 4-(HOCO)Ph | 0 |
| 82 | 3,4,5-triMeOPh | 4-(HOCO)Ph | 0 |
| 83 | 3,4,5-triMeOPh | 4-(MeOCO)Ph | 0 |
| 84 | 2,4,6-triMeOPh | 4-(HOCO)Ph | 0 |
| 85 | 2,4,6-triMeOPh | 4-(MeOCO)Ph | 0 |
| 86 | 4-MeOPh | 4-(MeOCO)Ph | 0 |
| 87 | 2-MeOPh | 4-(MeOCO)Ph | 0 |
| 88 | 2-MeOPh | 4-(EtOCO)Ph | 0 |
| 89 | 2-iPrOPh | 4-(HOCO)Ph | 0 |
| 90 | 4-NH₂Ph | 4-(HOCO)Ph | 0 |
| 91 | 3-NH₂Ph | 4-(HOCO)Ph | 0 |
| 92 | 2-NH₂Ph | 4-(HOCO)Ph | 0 |
| 93 | 2-OHPh | 4-(HOCO)Ph | 0 |
| 94 | 2-OHPh | 4-(MeOCO)Ph | 0 |
| 95 | 3-OHPh | 4-(HOCO)Ph | 0 |
| 96 | 4-OHPh | 4-(HOCO)Ph | 0 |
| 97 | 2,5-diOHPh | 4-(HOCO)Ph | 0 |
| 98 | 3,5-diOHPh | 4-(HOCO)Ph | 0 |
| 99 | 2,6-diOHPh | 4-(HOCO)Ph | 0 |
| 100 | 2,4,6-triOHPh | 4-(HOCO)Ph | 0 |
| 101 | 4-(HOCO)Ph | 4-(HOCO)Ph | 0 |
| 102 | 4-CarPh | 4-(HOCO)Ph | 0 |
| 103 | 4-CNPh | 4-(HOCO)Ph | 0 |
| 104 | 4-AcOPh | 4-(HOCO)Ph | 0 |
| 105 | 2-PhEt | 4-(HOCO)Ph | 0 |
| 106 | 2-(4-FPh)Et | 4-(HOCO)Ph | 0 |
| 107 | 2-(2-FPh)Et | 4-(HOCO)Ph | 0 |
| 108 | 2-(3-FPh)Et | 4-(HOCO)Ph | 0 |
| 109 | 2-(2,3-diFPh)Et | 4-(HOCO)Ph | 0 |
| 110 | 2-(2,4-diFPh)Et | 4-(HOCO)Ph | 0 |
| 111 | 2-(2,5-diFPh)Et | 4-(HOCO)Ph | 0 |
| 112 | 2-(2,6-diFPh)Et | 4-(HOCO)Ph | 0 |
| 113 | 2-(2-ClPh)Et | 4-(HOCO)Ph | 0 |
| 114 | 2-(3-ClPh)Et | 4-(HOCO)Ph | 0 |
| 115 | 2-(4-ClPh)Et | 4-(HOCO)Ph | 0 |
| 116 | 2-(4-ClPh)Et | 4-(MeOCO)Ph | 0 |
| 117 | 2-(2,6-diClPh)Et | 4-(HOCO)Ph | 0 |
| 118 | 2-(3-MeOPh)E | 4-(HOCO)Ph | 0 |
| 119 | 2-(4-MeOPh)Et | 4-(HOCO)Ph | 0 |
| 120 | 2-(2-MeOPh)Et | 4-(HOCO)Ph | 0 |
| 121 | 2-(2-MePh)Et | 4-(HOCO)Ph | 0 |
| 122 | 2-(3-MePh)Et | 4-(HOCO)Ph | 0 |
| 123 | 2-(4-MePh)Et | 4-(HOCO)Ph | 0 |
| 124 | 2-(2,3-diMeOPh)Et | 4-(HOCO)Ph | 0 |
| 125 | 2-(3,4-diMeOPh)Et | 4-(HOCO)Ph | 0 |
| 126 | 2-(2,4-diMeOPh)Et | 4-(HOCO)Ph | 0 |
| 127 | 2-(2,5-diMeOPh)Et | 4-(HOCO)Ph | 0 |
| 128 | 2-(2,6-diMeOPh)Et | 4-(HOCO)Ph | 0 |
| 129 | 2-(4-CF₃Ph)Et | 4-(HOCO)Ph | 0 |
| 130 | 2-(2-CF₃Ph)Et | 4-(HOCO)Ph | 0 |
| 131 | 2-(3-CF₃Ph)Et | 4-(HOCO)Ph | 0 |
| 132 | 2-(2,4,6-triMePh)Et | 4-(HOCO)Ph | 0 |
| 133 | 2-(3,4,5-triMeOPh)Et | 4-(HOCO)Ph | 0 |
| 134 | 2-(2,4-diMePh)Et | 4-(HOCO)Ph | 0 |

TABLE 1-continued

| Cpd No | R² | A | n |
|---|---|---|---|
| 135 | 2-(3,4-diMePh)Et | 4-(HOCO)Ph | 0 |
| 136 | 2-(2,5-diMePh)Et | 4-(HOCO)Ph | 0 |
| 137 | 4-FBz | 4-(HOCO)Ph | 0 |
| 138 | 3-FBz | 4-(HOCO)Ph | 0 |
| 139 | 4-ClBz | 4-(HOCO)Ph | 0 |
| 140 | 3-ClBz | 4-(HOCO)Ph | 0 |
| 141 | 2-MeBz | 4-(HOCO)Ph | 0 |
| 142 | 3-MeBz | 4-(HOCO)Ph | 0 |
| 143 | 4-MeBz | 4-(HOCO)Ph | 0 |
| 144 | 3,4-diMeBz | 4-(HOCO)Ph | 0 |
| 145 | 2-MeOBz | 4-(HOCO)Ph | 0 |
| 146 | 3-MeOBz | 4-(HOCO)Ph | 0 |
| 147 | 4-MeOBz | 4-(HOCO)Ph | 0 |
| 148 | 2,4-diMeOBz | 4-(HOCO)Ph | 0 |
| 149 | Bz | 4-(MeOCO)Ph | 0 |
| 150 | 2-PhEt | 4-(MeOCO)Ph | 0 |
| 151 | PhCH=CH— | 4-(HOCO)Ph | 0 |
| 152 | Ph | 4-HOCO—2-MePh | 0 |
| 153 | Ph | 4-HOCO—2-ClPh | 0 |
| 154 | Ph | 4-(MeOCO)—2-MePh | 0 |
| 155 | Ph | 4-(MeOCO)—2-ClPh | 0 |
| 156 | Ph | 4-CarPh | 0 |
| 157 | Ph | 4-(MeNHCO)Ph | 0 |
| 158 | 2-Pyr | 4-(HOCO)Ph | 0 |
| 159 | 4-Pyr | 4-(HOCO)Ph | 0 |
| 160 | 3-Pyr | 4-(HOCO)Ph | 0 |
| 161 | 3-Pyr | 4-(MeOCO)Ph | 0 |
| 162 | 2-Thi | 4-(HOCO)Ph | 0 |
| 163 | 2-Thi | 4-(MeOCO)Ph | 0 |
| 164 | 3-Thi | 4-(HOCO)Ph | 0 |
| 165 | 2-Fur | 4-(HOCO)Ph | 0 |
| 166 | 2-Fur | 4-(MeOCO)Ph | 0 |
| 167 | 2,5-diMe—3-Thi | 4-(HOCO)Ph | 0 |
| 168 | 2-Cl—5-Thi | 4-(HOCO)Ph | 0 |
| 169 | 3-Me—2-Thi | 4-(HOCO)Ph | 0 |
| 170 | 2-Me—5-Thi | 4-(HOCO)Ph | 0 |
| 171 | 3-Cl—2-Thi | 4-(HOCO)Ph | 0 |
| 172 | 2-Me—5-Fur | 4-(HOCO)Ph | 0 |
| 173 | 3-Me—2-Fur | 4-(HOCO)Ph | 0 |
| 174 | 3-Cl—2-Fur | 4-(HOCO)Ph | 0 |
| 175 | 4-Thiz | 4-(HOCO)Ph | 0 |
| 176 | 2-Pyz | 4-(HOCO)Ph | 0 |
| 177 | 1-Me—2-Pyrr | 4-(HOCO)Ph | 0 |
| 178 | 2-Thi—CH₂— | 4-(HOCO)Ph | 0 |
| 179 | 2-Fur—CH₂— | 4-(HOCO)Ph | 0 |
| 180 | 2-Pyr—CH₂— | 4-(HOCO)Ph | 0 |
| 181 | 2-(2-Thi)Et | 4-(HOCO)Ph | 0 |
| 182 | 2-(2-Fur)Et | 4-(HOCO)Ph | 0 |
| 183 | 2-(2-Pyr)Et | 4-(HOCO)Ph | 0 |
| 184 | 2-(3-Pyr)Et | 4-(HOCO)Ph | 0 |
| 185 | 2-(4-Pyr)Et | 4-(HOCO)Ph | 0 |
| 186 | 5-Pym—CH₂— | 4-(HOCO)Ph | 0 |
| 187 | 2-(2-Thiz)Et | 4-(HOCO)Ph | 0 |
| 188 | 1-ImidCH₂— | 4-(HOCO)Ph | 0 |
| 189 | 3-PyrCH₂— | 4-(HOCO)Ph | 0 |
| 190 | 4-PyrCH₂— | 4-(HOCO)Ph | 0 |
| 191 | 2-TrizCH₂— | 4-(HOCO)Ph | 0 |
| 192 | 2-Thf | 4-(HOCO)Ph | 0 |
| 193 | 2-Thp | 4-(HOCO)Ph | 0 |
| 194 | 2-Pyrd | 4-(HOCO)Ph | 0 |
| 195 | 3-Pip | 4-(HOCO)Ph | 0 |
| 196 | 4-Pip | 4-(HOCO)Ph | 0 |
| 197 | 2-Pip | 4-(HOCO)Ph | 0 |
| 198 | 2-(2-Thf)Et | 4-(HOCO)Ph | 0 |
| 199 | 2-(2-Thp)Et | 4-(HOCO)Ph | 0 |
| 200 | 1-PyrdCH₂— | 4-(HOCO)Ph | 0 |
| 201 | 1-PipCH₂— | 4-(HOCO)Ph | 0 |
| 202 | MorCH₂— | 4-(HOCO)Ph | 0 |
| 203 | 4-Ac—1-PizCH₂— | 4-(HOCO)Ph | 0 |
| 204 | 1-PizCH₂— | 4-(HOCO)Ph | 0 |
| 205 | ThzCH₂— | 4-(HOCO)Ph | 0 |
| 206 | 2-MorEt | 4-(HOCO)Ph | 0 |
| 207 | 4-CHO—1-Piz | 4-(HOCO)Ph | 0 |
| 208 | —COOH | 4-(HOCO)Ph | 0 |
| 209 | MeOCO— | 4-(HOCO)Ph | 0 |
| 210 | EtOCO— | 4-(HOCO)Ph | 0 |
| 211 | Car | 4-(HOCO)Ph | 0 |
| 212 | 2-AcOPh | 4-(HOCO)Ph | 0 |
| 213 | 4-(MeOCO)Ph | 4-(HOCO)Ph | 0 |
| 214 | 4-AcNHPh | 4-(HOCO)Ph | 0 |
| 215 | 4-MeSPh | 4-(HOCO)Ph | 0 |
| 216 | 4-MeSOPh | 4-(HOCO)Ph | 0 |
| 217 | 4-MeSO₂Ph | 4-(HOCO)Ph | 0 |
| 218 | 2-CF₃Ph | 2-Me-4-(HOCO)Ph | 0 |
| 219 | 2-CF₃Ph | 2-Cl—4-(HOCO)Ph | 0 |
| 220 | 2-MeOPh | 2-Me-4-(HOCO)Ph | 0 |
| 221 | 2-MeOPh | 2-Cl—4-(HOCO)Ph | 0 |
| 222 | 2-MePh | 2-Cl—4-(HOCO)Ph | 0 |
| 223 | 2-FPh | 2-Cl—4-(HOCO)Ph | 0 |
| 224 | 2-Fur | 2-Cl—4-(HOCO)Ph | 0 |
| 225 | 2-Thi | 2-Cl—4-(HOCO)Ph | 0 |
| 226 | 2-MePh | 2-Me—4-(HOCO)Ph | 0 |
| 227 | 2-FPh | 2-Me—4-(HOCO)Ph | 0 |
| 228 | 2-Fur | 2-Me—4-(HOCO)Ph | 0 |
| 229 | 2-Thi | 2-Me—4-(HOCO)Ph | 0 |
| 230 | 2-MeOPh | 4-CarPh | 0 |
| 231 | 2-MePh | 4-CarPh | 0 |
| 232 | 2-CF₃Ph | 4-CarPh | 0 |
| 233 | 2-Fur | 4-CarPh | 0 |
| 234 | 2-MeOPh | 4-(HOCO)Ph | 1 |
| 235 | 2-MeOPh | 4-(MeOCO)Ph | 1 |
| 236 | 2-MeOPh | 4-(HOCO)Ph | 2 |
| 237 | 2-MeOPh | 4-(MeOCO)Ph | 2 |
| 238 | 2-MePh | 4-(HOCO)Ph | 1 |
| 239 | 2-MePh | 4-(HOCO)Ph | 2 |
| 240 | 2-CF₃Ph | 4-(HOCO)Ph | 1 |
| 241 | 2-CF₃Ph | 4-(HOCO)Ph | 2 |
| 242 | Ph | 4-(tBuOCOCH₂OCO)Ph | 0 |
| 243 | 2-MePh | 4-(tBuOCOCH₂OCO)Ph | 0 |
| 244 | 2-MeOPh | 4-(tBuOCOCH₂OCO)Ph | 0 |
| 245 | Ph | 4-[1-(EtO.CO.O)EtOCO]Ph | 0 |
| 246 | 2-MePh | 4-[1-(EtO.CO.O)EtOCO]Ph | 0 |
| 247 | 2-MeOPh | 4-[1-(EtO.CO.O)EtOCO]Ph | 0 |
| 248 | Ph | 4-(PhthOCO)Ph | 0 |
| 249 | 2-MePh | 4-(PhthOCO)Ph | 0 |
| 250 | 2-MeOPh | 4-(PhthOCO)Ph | 0 |
| 251 | Ph | 4-(DoxOCO)Ph | 0 |
| 252 | 2-MePh | 4-(DoxOCO)Ph | 0 |
| 253 | 2-MeOPh | 4-(DoxOCO)Ph | 0 |

Compounds of formula (I-2):

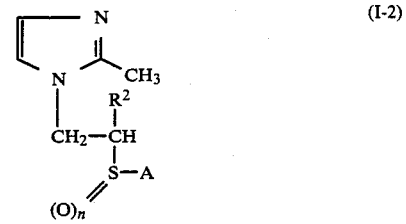

(I-2)

are as defined in Table 2:

TABLE 2

| Cpd No | R² | A | n |
|---|---|---|---|
| 254 | Ph | 4-(HOCO)Ph | 0 |
| 255 | Ph | 4-(MeOCO)Ph | 0 |
| 256 | 2-MePh | 4-(HOCO)Ph | 0 |
| 257 | 2-MePh | 4-(MeOCO)Ph | 0 |
| 258 | 2-MeOPh | 4-(HOCO)Ph | 0 |
| 259 | 2-MeOPh | 4-(MeOCO)Ph | 0 |

Compounds of formula (I-3):

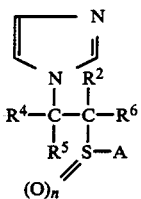

(I-3)

are as defined in Table 3:

TABLE 3

| Cpd No | R² | R⁴ | R⁵ | R⁶ | n | A |
|---|---|---|---|---|---|---|
| 260 | H | 2-FPh | H | H | 0 | 4-(HOCO)Ph |
| 261 | H | Ph | H | H | 0 | 2-Cl—4-(HOCO)Ph |
| 262 | H | Ph | H | H | 0 | 2-Me—4-(HOCO)Ph |
| 263 | H | 4-MePh | H | H | 0 | 4-(HOCO)Ph |
| 264 | H | 4-MeOPh | H | H | 0 | 4-(HOCO)Ph |
| 265 | H | 4-FPh | H | H | 0 | 4-(HOCO)Ph |
| 266 | Me | Ph | H | H | 0 | 4-(HOCO)Ph |
| 267 | 2-MeOPh | H | H | Me | 0 | 4-(HOCO)Ph |
| 268 | 2-MeOPh | H | H | Me | 0 | 4-(MeOCO)Ph |
| 269 | 2-MeOPh | H | H | Me | 1 | 4-(HOCO)Ph |
| 270 | 2-MeOPh | Me | Me | H | 0 | 4-(HOCO)Ph |
| 271 | 2-MeOPh | Me | H | H | 0 | 4-(HOCO)Ph |
| 272 | 2-MeOPh | H | H | All | 0 | 4-(HOCO)Ph |
| 273 | H | Ph | H | H | 0 | 4-(HOCO)Ph |
| 274 | H | Bz | H | H | 0 | 4-(HOCO)Ph |
| 275 | H | 2-Thi | H | H | 0 | 4-(HOCO)Ph |
| 276 | H | 2-Fur | H | H | 0 | 4-(HOCO)Ph |
| 277 | 2-MeOPh | All | H | H | 0 | 4-(HOCO)Ph |
| 278 | 2-MeOPh | Prg | H | H | 0 | 4-(HOCO)Ph |
| 279 | H | 2-MeOPh | H | H | 0 | 4-(HOCO)Ph |
| 280 | H | 2-MePh | H | H | 0 | 4-(HOCO)Ph |

Of the compounds listed above, the preferred compounds are Compounds No. 40, 44, 49, 58, 62, 66, 70, 74, 79, 84, 93, 115, 162 and 165, as well as their hydrochlorides and sodium salts.

The compounds of the present invention may be prepared by the processes described below.

Process A

In this process, a 2-imidazolylethyl derivative of formula (II) is reacted with a phenyl mercaptan of formula (III) to give a compound of formula (Ia) and then this is, if desired, oxidized to give a corresponding sulfinyl or sulfonyl compound of formula (Ib), as illustrated by the following reaction scheme:

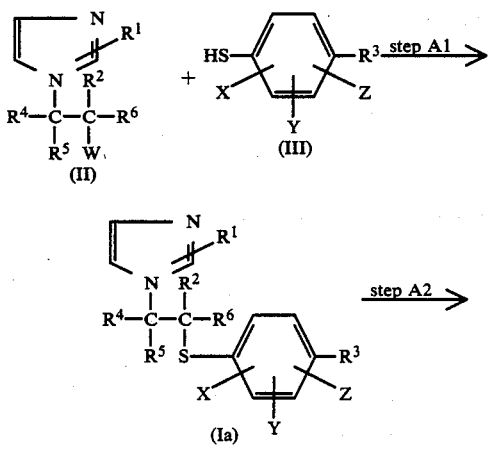

-continued

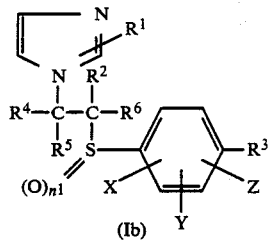

(Ib)

In the above formulae, R¹, R², R⁴, R⁵, R⁶, X, Y and Z are all as defined above. R³ represents a carboxy group or an esterified, amidified or salified carboxy group. n' represents the integer 1 or 2. W represents a leaving group.

The nature of the group represented by W is not critical in the present invention and any group which can be readily replaced by the thio group derived from the compound of formula (III) can be employed. Examples of suitable leaving groups include: the hydroxy group; halogen atoms, for example the chlorine, bromine or iodine atoms; $C_1$–$C_4$, and especially $C_1$ and $C_2$, alkanesulfonyloxy groups, such as the methanesulfonyloxy and ethanesulfonyloxy groups; trihalomethanesulfonyloxy groups, e.g. the trifluoromethanesulfonyloxy group; and arylsulfonyloxy groups, e.g. the benzenesulfonyloxy or p-toluenesulfonyloxy group.

In step A1 of this reaction, the 2-imidazolylethyl derivative of formula (II) is reacted with the phenyl mercaptan of formula (III) or with a salt thereof, to give the desired compound of formula (Ia).

This reaction is preferably effected in the presence of a solvent, the nature of which is not critical, provided that it has no adverse effect upon the reaction. Suitable solvents include halogenated hydrocarbons, especially halogenated aliphatic hydrocarbons, such as chloroform, methylene chloride or 1,2-dichloroethane; ketones, such as acetone or methyl ethyl ketone; ethers, such as diethyl ether, tetrahydrofuran or dioxane; aromatic hydrocarbons, such as benzene or toluene; esters, such as ethyl formate or ethyl acetate; alcohols, such as methanol or ethanol; amides, such as dimethylformamide or dimethylacetamide; dimethyl sulfoxide; nitromethane; a mixture of any two or more of the above organic solvents; or a mixture of any one of more of the above organic solvents with water.

The reaction is preferably effected in the presence of an acid-binding agent, particularly where W represents a halogen atom or a sulfonyloxy group. The function of the acid-binding agent is to remove from the reaction the acid liberated by the condensation and, accordingly, any basic compound which will serve this function may be employed. Suitable bases include: amines, such as triethylamine, pyridine, 2,6-lutidine, or dimethylaniline; alkali metal bicarbonates, such as sodium bicarbonate; alkali metal and alkaline earth metal carbonates, such as sodium carbonate, potassium carbonate or calcium carbonate; and alkali metal hydroxides, such as sodium hydroxide or potassium hydroxide.

We find it particularly convenient first to convert the phenyl mercaptan (III) to its salt with an alkali or alkaline earth metal or with an organic base before reaction with the imidazolylethyl compound of formula (II).

Where W represents a hydroxy group, the reaction may also be effected in the presence of a suitable acidic compound, for example: a mineral acid, such as sulfuric acid, hydrochloric acid or hydrobromic acid; an organic carboxylic or sulfonic acid, such as trifluoroacetic acid, acetic acid or p-toluenesulfonic acid; or a Lewis acid, such as boron trifluoride diethyl etherate. The reaction may also be effected in the presence of a condensing agent, for example a combination of diethyl azodicarboxylate with triphenylphosphine.

The reaction involved in step A1 will take place over a wide range of temperatures and the temperature employed is not particularly critical. However, in order to suppress side reactions, it is desirable that the temperature should not be too high and, accordingly, a temperature of from $-10°$ C. to $+100°$ C. is normally preferred. The time required for the reaction will vary widely, depending upon many factors, including the nature of the starting materials and the reaction temperature, but a period of from 20 minutes to 100 hours will normally suffice.

In step A2, if desired, the thio compound of formula (Ia) is converted to the corresponding S-oxide or S,S-dioxide, i.e. the corresponding sulfinyl or sulfonyl derivative, respectively, by oxidation.

The oxidation reaction is preferably effected in the presence of an inert solvent using any conventional oxidizing agent. There is no particular limitation to be imposed on the choice of oxidizing agent, provided that it is capable of oxidizing thio compounds to sulfinyl and/or sulfonyl compounds, without affecting the remainder of the molecule. Suitable oxidizing agents are the organic peracids, particularly m-chloroperbenzoic acid and peracetic acid.

The solvent to be employed is likewise not critical, provided that it has no adverse effect on the reaction. Examples of suitable solvents include: halogenated hydrocarbons, particularly halogenated aliphatic hydrocarbons, such as methylene chloride or chloroform; ethers, such as tetrahydrofuran or dioxane; organic acids, such as acetic acid; or a mixture of one or more such organic solvents with water.

Although the reaction temperature is not particularly critical, a relatively low temperature is generally preferred, in order to avoid undesirable side reactions, and we therefore normally prefer a temperature within the range from $0°$ C. to room temperature. The time required for the reaction will vary widely, depending upon many factors, notably the reaction temperature and the nature of the starting material, but a period of from 20 minutes to 50 hours will normally suffice.

If the compound of formula (Ia) contains an alkylthio group [i.e. if substituent (a), X, Y or Z represents an alkylthio group], then this may simultaneously be oxidized to the corresponding alkylsulfinyl or alkylsulfonyl group.

Step A2 of this reaction sequence may be carried out with or without intermediate isolation of the product of step A1, the thio compound of formula (Ia). After either or both of steps A1 and A2, the product of the reaction may be isolated from the reaction mixture by conventional means. For example, one suitable recovery sequence, which may be employed for either step, comprises: adding a water-immiscible organic solvent to the reaction mixture; separating the organic phase, containing the desired compound, from the mixture; if necessary, washing the separated organic phase with water; and then distilling off the solvent, to give the desired product of formula (Ia) or (Ib). This product may, if necessary, be further purified by conventional means, for example recrystallization, reprecipitation or the various chromatography techniques, particularly column chromatography or preparative thin layer chormatography.

Process B

In this process, imidazole or an imidazole derivative of formula (IV) is reacted with a 2-phenylthioethyl derivative of formula (V), to give a compound of formula (Ic), and then this is, if necessary, oxidized to give a compound of formula (Id), as illustrated in the following reaction scheme:

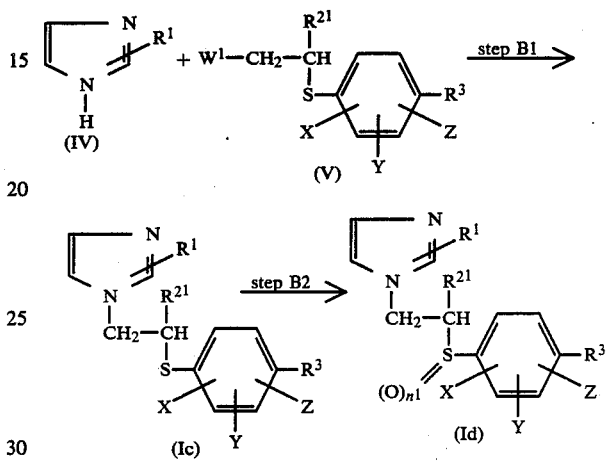

In the above formulae, $R^1$, $R^3$, X, Y, Z and n' are as defined above. $R^{2'}$ represents any one of the groups represented by $R^2$, but not a hydrogen atom, and W' represents a leaving group, examples of which are the same as given in relation to W, but not including the hydroxy group.

In step B1 of this reaction, the imidazole or derivative thereof of formula (IV) or an alkali metal salt thereof is reacted with the 2-phenylthioethyl derivative of formula (V) to give the compound of formula (Ic).

If it is desired that the imidazole compound of formula (IV) should be used in the form of an alkali metal salt, then the imidazole is first reacted with an alkali metal hydride, (e.g. sodium hydride or potassium hydride) in a suitable inert solvent.

The reaction of the imidazole compound (IV) or its salt with the phenylthioethyl compound (V) is preferably effected in the presence of a solvent. The nature of the solvent is not critical, provided that it has no adverse effect on the reaction. Suitable solvents include, for example: ethers, such as diethyl ether, tetrahydrofuran or dioxane; aromatic hydrocarbons, such as benzene or toluene; halogenated hydrocarbons, particularly halogenated aliphatic hydrocarbons, such as methylene chloride, chloroform or 1,2-dichloroethane; amides, such as hexamethylphosphoric triamide, dimethylacetamide or dimethylformamide; alcohols, such as methanol or ethanol; ketones, such as acetone or methyl ethyl ketone; nitriles, such as acetonitrile; esters, such as ethyl formate or ethyl acetate; dimethyl sulfoxide; nitromethane; and mixtures of any two or more of these organic solvents.

The reaction temperature is not particularly critical and the reaction of step B1 will take place over a wide range of temperatures. However, in order to suppress side reactions, it is desirable that the temperature should not be too high and, accordingly, a temperature within the range from −10° C. to +100° C. is normally preferred. The time required for the reaction will vary widely, depending upon many factors, notably the reaction temperature and the nature of the starting materials, but a period of from 20 minutes to 100 hours will normally suffice.

If desired, the resulting product of formula (Ic) may then be subjected to step B2, which is an oxidation step identical with step A2, and which may be carried out employing the same reagents and under the same reaction conditions.

After either or both of steps B1 and B2, the desired product may be separated from the reaction mixture by conventional means. For example, one suitable recovery technique comprises: adding a water-immiscible organic solvent to the reaction mixture; separating the organic phase and, if necessary, washing it with water; and distilling off the solvent to leave the desired product—the compound of formula (Ic) or (Id). This may, if necessary, be further purified by conventional means, for example recrystallization, reprecipitation or the various chromatography techniques, such as column chromatography or preparative thin layer chromatography.

If $R^2$, substituent (a) or $R^3$ in the resulting compound of formula (Ia), (Ib), (Ic) or (Id) represents an esterified carboxy group, this may, if desired, be de-esterified, to give a free carboxy group, by known means. For example, if it is a straight chain alkyl ester, such as a methyl or ethyl ester, the alkyl group may be removed by alkaline hydrolysis. If it is a t-butyl ester, the t-butyl group may be removed by treatment with trifluoroacetic acid. If it is an aralkyl ester (such as a benzyl or p-nitrobenzyl ester) or a benzhydryl ester, then the aralkyl or benzhydryl group may be removed by treatment with a reducing agent. These reactions are preferably effected in the presence of a solvent, the nature of which is not critical, provided that it does not adversely affect the reaction. Suitable solvents include, for example: alcohols, such as methanol or ethanol; ethers, such as tetrahydrofuran or dioxane; and mixtures of any one or more of these organic solvents with water. The reaction temperature is not particularly critical and may vary wide, for example from 0° to 100° C. The time required for the reaction will vary depending upon many factors, notably the nature of the starting materials and reagents (such as alkalis or reducing agents) used for removal of the ester group, but a period of from 5 minutes to 12 hours will normally suffice.

After completion of this reaction, the resulting carboxylic acid can, if desired, be separated from the reaction mixture by conventional means. For example, one suitable recovery technique comprises: if necessary, filtering off any insoluble substances; washing the organic solvent layer with water and then drying it; and distilling off the solvent to give the desired compound. This can, if required, be further purified by conventional means, for example recrystallization or the various chromatography techniques, such as preparative thin layer chromatography or column chromatography.

Where $R^2$, substituent (a) or $R^3$ represents a carboxy or esterified carboxy group, this can be converted into another esterified carboxy group or into a carbamoyl or N-substituted or N,N-disubstituted carbamoyl group by conventional means.

Similarly, the compounds of the invention can be converted to their pharmaceutically acceptable salts by treatment with an acid or a base, as is well-known in the art.

The compounds of the present invention have been found, as demonstrated hereafter, to inhibit the activity of $TXA_2$ synthetase, as a result of which they have an antithrombotic activity, as also demonstrated hereafter.

Inhibition of Thromboxane $A_2$ Synthetase

The platelet microsome fraction was separated from rabbit and from human blood by the method of Needleman et al. [Needleman et al., Science, 193, 163 (1976)].

The microsomal $TXA_2$ synthetase activity in the presence of various of the compounds of the invention at various concentrations was assayed by a modification of the method of Kayama et al. [Kayama et al., Prostaglandins, 21, 543 (1981)] by incubating the microsome fractions with labelled 1-[$^{14}C$] arachidonic acid at a concentration of 0.1 mM for 1 minute at 22° C., to a final volume of 0.2 ml. The reaction was terminated by the addition of 50 μM of 0.2M citric acid, and then the mixture was extracted with 1.5 ml of ethyl acetate. The extract was concentrated under a stream of nitrogen gas and then subjected to silica gel thin layer chromatography. The developing solvent for the chromatography was a 90:8:1:0.8 by volume mixture of chloroform, methanol, acetic acid and water. The inhibitory activity of the compound tested was estimated by the decrease in the radioactivity of the $TXB_2$ fraction ($TXA_2$ is hydrolysed to the more stable $TXB_2$). The results are shown in the following Table as the $IC_{50}$, i.e. the concentration required to inhibit the activity of thromboxane synthetase by 50%.

In addition to the compounds of the invention, we also tested the activity of the known compound Dazoxiben, whose systematic name is 4-[2-(1-imidazolyl)ethoxy]benzoic acid hydrochloride, and which is disclosed in GB Patent Specification No. 2,038,821. The compounds of the invention are identified in the following Tables by the numbers heretofore assigned to them. All compounds were employed in the form of the hydrochloride, except Compound No. 40, which was employed as the free base.

The results using rabbit platelet microsomes are given in Table 4, whilst the results using human platelet microsomes are given in Table 5.

TABLE 4

| Test Compound - Cpd. No. | $IC_{50}$ ($\times 10^{-8}$ M) |
|---|---|
| 40 | 7.1 |
| 44 | 4.7 |
| 49 | 8.1 |
| 58 | 6.7 |
| 62 | 6.9 |
| 70 | 5.9 |
| 74 | 4.0 |
| 79 | 5.7 |
| 84 | 3.3 |
| Dazoxiben | 10.6 |

TABLE 5

| Test Compound - Cpd. No. | $IC_{50}$ ($\times 10^{-8}$M) |
|---|---|
| 58 | 5.2 |
| 70 | 7.3 |
| Dazoxiben | 76 |

As can be seen from the results given above, the compounds of the invention show a significantly greater activity than does the known compound Dazoxiben and, in particular, as shown in Table 5, the activity of the compounds of the invention against thromboxane synthetase derived from human platelet microsomes is about 10 times higher than the activity of Dazoxiben.

Antithrombotic Activity in Rabbits

This test was carried out by a modification of the method of Silver et al. [Science, 183, 1085 (1974)]. The test animals used were male Japanese white rabbits of approximately 3 kg bodyweight.

Each group of rabbits was administered orally the test compound at an appropriate dose and then, one hour after the oral administration, each was given 1.3 mg/kg or arachidonic acid by intravenous injection. The test animals were observed and sudden deaths during the test period were recorded. The $ED_{50}$ was determined by Probit's method.

Unmedicated rabbits were employed as a control, without administering any test compound, but these were all dead within several minutes after the injection of arachidonic acid, as a result of pulmonary thromboembolisms.

The results, in terms of the $ED_{50}$, are given in the following Table 6.

TABLE 6

| Test Compound | $ED_{50}$ (mg/kg) |
|---|---|
| Cpd No. 70 | 0.13 |
| Dazoxiben | 1.1 |

The results given above indicate an activity about 10 times higher than that of the known compound Dazoxiben.

The results given above demonstrate that the compounds of the invention inhibit thromboxane synthetase of the blood platelet microsomes of mammals, including humans, and that they further exhibit strong and specific inhibitory activities against the biosynthesis of $TXA_2$. Specifically, the biosynthesis of $TXA_2$ may be inhibited to the extent of 50% by a concentration of the compound of the order of $10^{-8}$ molar. However, the compounds of the invention have very weak inhibitory activities against cyclooxigenase and against prostacyclin synthetase and thus do not inhibit the synthesis of other prostaglandin derivatives.

Also, we have demonstrated in in vivo tests that the compounds of the invention exhibit via oral administration an inhibitory effect against pulmonary thromboembolisms in rabbits and mice caused by the intravenous injection of arachidonic acid.

Accordingly, the compounds of the present invention are expected to be valuable for the therapy and prophylaxis of diseases and disorders caused by an imbalance in the blood level of $TXA_2$, for example inflammation, hypertension, thrombosis, cerebral haemorrhages and asthma and are expected to be especially useful in the treatment of prophylaxis of thromboembolisms in mammals, including humans. For example, they are expected to be useful in the treatment and prophylaxis of myocardial infarction, cerebral vascular thrombosis and ischemic peripheral blood vessel diseases, as well as in the treatment and prophylaxis of postoperative thrombosis and to accelerate the dilation of transplanted blood vessels after an operation.

The compounds of the invention may be administered by any suitable route, oral or parenteral and may be formulated accordingly, for example: for oral administration as tablets, capsules, powders or syrups; or, for parenteral administration, as suppositories or as injectible solutions or suspensions for subcutaneous or intravenous injection.

The compounds of the invention may be formulated with conventional pharmaceutical carriers or diluents or may be administered as such.

The amount of the compound of the invention to be administered will vary, depending upon the nature and severity of the disease or disorder to be treated, the age, bodyweight, symptoms and condition of the patient and the mode of administration. However, by way of guidance, the dose for an adult human being would be expected to be from 50 to 1800 mg per day, which is preferably administered in divided doses, e.g. about 3 times per day.

The preparation of certain compounds of the invention is further illustrated by the following Examples.

EXAMPLE 1

Methyl 4-[1-phenyl-2-(imidazol-1-yl)ethylthio]benzoate 1.5 g of methyl 4-mercaptobenzoate was dissolved in 8 ml of dry dimethylformamide, and the resulting solution was added to 388 mg of a 55% w/w suspension of sodium hydride in mineral oil, whilst ice-cooling, and then the mixture was stirred at room temperature for 30 minutes. A solution of 1.5 g of 1-(2-chloro-2-phenylethyl)imidazole dissolved in 8 ml of dry dimethylformamide was added to the thus obtained solution, and the mixture was then heated at 65° to 70° C. for 6 hours. At the end of this time, the reaction mixture was poured into a saturated aqueous solution of sodium chloride, and the resulting solution was extracted with diethyl ether. The extract was washed with water and dried over anhydrous potassium carbonate, and then the solvent was removed by distillation. The residue was purified by column chromatography through silica gel (eluent: ethyl acetate:triethylamine=40:1 by volume) to obtain 747 mg of the title compound as a colorless powder.

Infrared Absorption Spectrum (Nujol-trade mark) $v_{max}cm^{-1}$: 1730, 1595, 1555, 1510.

Nuclear Magnetic Resonance Spectrum (CDCl$_3$) δ ppm: 3.84 (3H, singlet); 4.10–4.46 (3H, multiplet); 6.57 (1H, singlet); 6.83 (1H, singlet); 6.88–7.35 (8H, multiplet); 7.80 (2H, doublet, J=8.0 Hz).

EXAMPLE 2

4-[1-Phenyl-2-(imidazol-1-yl)ethylthio]benzoic acid and its hydrochloride (a) 603 mg of methyl 4-[1-phenyl-2-(imidazol-1-yl)ethylthio]benzoate (prepared as described in Example 1) were dissolved in 7.1 ml of methanol and 7.1 ml of a 1N aqueous solution of sodium hydroxide was added to the resulting solution. The resulting mixture was stirred at room temperature for 1 hour, followed by heating under reflux for 1 hour. The solvent was then removed by distillation, and 1.8 ml of a 1N aqueous solution of sodium hydride was added to the residue. The resulting mixture was extracted with chloroform, and then the aqueous layer was made acidic (pH 2 to 3) with 6N aqueous hydrochloric acid. The resulting mixture was extracted with chloroform, and the aqueous layer was then neutralized with concentrated aqueous ammonia. The resulting solution, which was turbid white, was extracted with chloroform and dried over anhydrous magnesium sulfate. The solvent was removed by distillation to give 182 mg of the title compound (free base) as a colorless powder.

Infrared Absorption Spectrum (KBr) $\nu_{max}$cm$^{-1}$: 3400, 1690, 1590, 1560, 1505.

Nuclear Magnetic Resonance Spectrum (CDCl$_3$) δ ppm: 4.12–4.70 (3H, multiplet); 6.65 (1H, singlet); 7.00 (1H, singlet); 7.06–7.46 (7H, multiplet); 7.63 (1H, singlet); 7.98 (2H, doublet, J=8.0 Hz); 11.20 (1H, broad singlet).

(b) 30 mg of 4-[1-phenyl-2-(imidazol-1-yl)ethylthio]benzoic acid were dissolved in 2 ml of chloroform. 4 ml of diethyl ether saturated with hydrogen chloride gas and 20 ml of diethyl ether were successively added to the resulting solution. Then the diethyl ether was decanted off and the precipitate was washed with diethyl ether. The resulting crystals were collected by filtration to give 28 mg of the hydrochloride of the title compound, melting at 117° to 120° C.

EXAMPLE 3

Methyl 4-[1-(2,4-dichlorophenyl)-2-(imidazol-1-yl)ethylthio]benzoate 415 mg of methyl 4-mercaptobenzoate were dissolved in 3 ml of dry dimethylformamide, and 108 mg of a 55% w/w suspension of sodium hydride in mineral oil were then added to the resulting solution, whilst ice-cooling, after which the mixture was stirred at room temperature for 30 minutes. 567 mg of a solution of 1-[2-chloro-2-(2,4-dichlorophenyl)ethyl]imidazole dissolved in 3 ml of dry dimethylformamide were then added to the resulting solution, and the mixture was heated at 60° to 70° C. for 7 hours. At the end of this time, the resulting mixture was treated and purified similarly to the procedure described in Example 1, to give 317 mg of the title compound as colorless crystals, melting at 121°–124° C.

Infrared Absorption Spectrum (Nujol) $\nu_{max}$cm$^{-1}$: 1718, 1585, 1560, 1505.

Nuclear Magnetic Resonance Spectrum (CDCl$_3$) δ ppm: 3.86 (3H, singlet); 4.34 (2H, doublet, J=7.0 Hz); 5.13 (1H, triplet, J=7.0 Hz); 6.72–7.46 (8H, multiplet); 7.88 (2H, doublet, J=8.0 Hz).

EXAMPLE 4

4-[1-(2,4-Dichlorophenyl)-2-(imidazol-1-yl)ethylthio]benzoic acid hydrochloride 306 mg of methyl 4-[1-(2,4-dichlorophenyl)-2-(imidazol-1-yl)ethylthio]benzoate (prepared as described in Example 3) were dissolved in 4 ml of methanol. 3 ml of a 1N aqueous solution of sodium hydroxide was added to the resulting solution, and the mixture was stirred at room temperature for 5 hours, and was then heated under reflux for 1 hour. The solvent was removed by distillation, and 1.5 ml of a 1N aqueous solution of sodium hydroxide was added to the residue. The resulting mixture was extracted with chloroform, and the aqueous layer was acidified (pH value 2 to 3) with 6N aqueous hydrochloric acid. The crystals which precipitated were collected by filtration, washed with water and dried, followed by recrystallization from a mixture of ethanol and ethyl acetate, to give 191 mg of the title compound as colorless crystals, melting at 187°–190° C.

Infrared Absorption Spectrum (KBr) $\nu_{max}$cm$^{-1}$: 3400, 1715, 1700, 1590, 1565, 1540.

Nuclear Magnetic Resonance Spectrum [(CD$_3$)$_2$SO] δ ppm: 4.95 (2H, doublet, J=7.0 Hz); 5.49 (1H, triplet, J=7.0 Hz); 7.43–8.00 (9H, multiplet); 9.35 (1H, singlet).

EXAMPLE 5

Methyl 4-[1-(4-fluorophenyl)-2-(imidazol-1-yl)ethylthio]benzoate 965 mg of methyl 4-mercaptobenzoate were dissolved in 6 ml of dry dimethylformamide. 250 mg of a 55% w/w suspension of sodium hydride in mineral oil were added to the resulting solution, whilst ice-cooling, and the mixture was then stirred at room temperature for 30 minutes. A solution of 1.1 g of 1-[2-chloro-2-(4-fluorophenyl)ethyl]imidazole dissolved in 16 ml of dry dimethylformamide was added to the resulting mixture. The mixture was then heated at 70° to 75° C. for 2.5 hours. At the end of this time, the resulting mixture was treated and purified similarly to the procedure described in Example 1, to give 866 mg of the title compound as a powder.

Infrared Absorption Spectrum (Nujol) $\nu_{max}$cm$^{-1}$: 1715, 1595, 1560, 1510.

Nuclear Magnetic Resonance Spectrum (CDCl$_3$) δ ppm: 3.85 (3H, singlet); 4.16–4.60 (3H, multiplet); 6.55–7.45 (9H, multiplet); 7.82 (2H, doublet, J=8.0 Hz).

EXAMPLE 6

4-[1-(4-Fluorophenyl)-2-(imidazol-1-yl)ethylthio]benzoic acid hydrochloride 841 mg of methyl 4-[1-(4-fluorophenyl)-2-(imidazol-1-yl)ethylthio]benzoate (prepared as described in Example 5) were dissolved in 9.4 ml of methanol. 9.4 ml of a 1N aqueous solution of sodium hydroxide were then added to the resulting solution, and the mixture obtained was stirred at room temperature for 1 hour, followed by heating under reflux for 3.5 hours. The solvent was then removed by distillation, and 4.5 ml of a 1N aqueous solution of sodium hydroxide were added to the residue. The resulting mixture was extracted with chloroform, and the aqueous layer was acidified (pH value 2 to 3) with 6N aqueous hydrochloric acid. The crystals which precipitated were collected by filtration, washed with water and dried, followed by recrystallization from a mixture of ethanol and ethyl acetate, to give 682 mg of the title compound as colorless crystals, melting at 226°–230° C.

Infrared Absorption Spectrum (Nujol) $\nu_{max}$cm$^{-1}$: 1685, 1590, 1560, 1540, 1505.

Nuclear Magnetic Resonance Spectrum [(CD$_3$)$_2$SO] δ ppm: 4.74 (2H, doublet, J=7.0 Hz); 5.35 (1H, triplet, J=7.0 Hz); 6.88–7.92 (10H, multiplet); 9.19 (1H, singlet).

EXAMPLE 7

Methyl 4-[1-(2-thienyl)-2-(imidazol-1-yl)ethylthio]benzoate 204 mg of methyl 4-mercaptobenzoate were dissolved in 1.3 ml of dry dimethylformamide, and 53 mg of a 55% w/w suspension of sodium hydride in mineral oil were added to the resulting solution, whilst ice-cooling. The mixture was then stirred at room temperature for 30 minutes. 258 mg of 1-[2-chloro-2-(2-thienyl)ethyl]imidazole dissolved in 1.3 ml of dry dimethylformamide were added to the resulting solution, and the mixture was then heated at 60° to 70° C. for 8 hours. At the end of this time, the resulting mixture was treated and purified similarly to the procedure described in Example 1, to give 20 mg of the title compound as an oil.

Nuclear Magnetic Resonance Spectrum (CDCl$_3$) δ ppm: 3.86 (3H, singlet); 4.16–4.82 (3H, multiplet); 6.55–7.42 (8H, multiplet); 7.84 (2H, doublet, J=8.0 Hz).

EXAMPLE 8

Sodium 4-[1-(2-thienyl)-2-(imidazol-1-yl)ethylthio]benzoate 20 mg of methyl 4-[1-(2-thienyl)-2-(imidazol-1-yl)ethylthio]benzoate (prepared as described in Example 7) were dissolved in 116 μl of methanol, and 116 μl of a 1N aqueous solution of sodium hydroxide were added to the resulting solution. The mixture was then stirred at room temperature for 3 hours. The methanol was removed from the reaction mixture by distillation under reduced pressure, and the remaining solution was subjected to chromatography through a Lobar column (LiChroprep, trade mark, RP-8, size B, produced by Merck) to give 7 mg of the title compound as a colorless powder from the portion eluted with 30% v/v aqueous methanol.

Infrared Absorption Spectrum (KBr) $v_{max}$cm$^{-1}$: 3400, 1590, 1545, 1505.

Nuclear Magnetic Resonance Spectrum (270 MHz, D$_2$O) δ ppm: 4.35 (2H, doublet, J=6.8 Hz); 4.83 (1H, triplet, J=6.8 Hz); 6.72 (1H, singlet); 6.86 (1H, singlet); 6.94 (1H, doublet, J=5.1 Hz); 7.01 (1H, singlet); 7.22 (2H, doublet, J=8.1 Hz); 7.27 (1H, doublet, J=5.1 Hz); 7.36 (1H, singlet); 7.56 (2H, doublet, J=8.1 Hz).

EXAMPLE 9

Methyl 4-[1-(2-methoxyphenyl)-2-(imidazol-1-yl)ethylthio]benzoate 915 mg of methyl 4-mercaptobenzoate were dissolved in 6 ml of dry dimethylformamide, and 237 mg of a 55% w/w suspension of sodium hydride in mineral oil were added, whilst ice-cooling, to the resulting solution, followed by stirring at room temperature for 30 minutes. A solution of 1.17 g of 1-[2-chloro-2-(2-methoxyphenyl)ethyl]imidazole dissolved in 6 ml of dry dimethylformamide was added to the resulting solution. At the end of this time, the resulting mixture was treated and purified similarly to the procedure described in Example 1, to give 1.26 g of the title compound as an oil.

Infrared Absorption Spectrum (liquid film) $v_{max}$cm$^{-1}$: 1715, 1595, 1560, 1505.

Nuclear Magnetic Resonance Spectrum (CDCl$_3$) δ ppm: 3.76 (3H, singlet); 3.84 (3H, singlet); 4.30 (2H, doublet, J=7.0 Hz); 5.02 (1H, triplet, J=7.0 Hz); 6.60–7.36 (9H, multiplet); 7.80 (2H, doublet, J=8.0 Hz).

EXAMPLE 10

4-[1-(2-Methoxyphenyl)-2-(imidazol-1-yl)ethylthio]benzoic acid hydrochloride 1.24 g of methyl 4-[1-(2-methoxyphenyl)-2-(imidazol-1-yl)ethylthio]benzoate (prepared as described in Example 9) was dissolved in 14 ml of methanol. 14 ml of a 1N aqueous solution of sodium hydroxide were added to the resulting solution and the mixture obtained was stirred at room temperature for 3 hours. The solvent was removed by distillation, and 7 ml of sodium hydroxide were added to the residue. The resulting mixture was extracted with chloroform, and the aqueous layer was acidified (pH 2 to 3) with 6N aqueous hydrochloric acid. The crystals which precipitated were collected by filtration, washed with water and dried, followed by recrystallization from a mixture of ethanol and diisopropyl ether, to give 1.15 g of the title compound as colorless crystals, melting at 140°–145° C.

Infrared Absorption Spectrum (KBr) $v_{max}$cm$^{-1}$: 3400, 1705, 1595, 1545, 1495.

Nuclear Magnetic Resonance Spectrum [(CD$_3$)$_2$SO] δ ppm: 3.84 (3H, singlet); 4.83 (2H, doublet, J=7.0 Hz); 5.37 (1H, triplet, J=7.0 Hz); 6.80–7.64 (7H, multiplet); 7.70 (1H, singlet); 7.87 (2H, doublet, J=8.0 Hz); 9.20 (1H, singlet).

EXAMPLE 11

Methyl 4-[1-(2,4,6-trimethylphenyl)-2-(imidazol-1-yl)ethylthio]benzoate 947 mg of methyl 4-mercaptobenzoate were dissolved in 6 ml of dry dimethylformamide, and 245 mg of a 55% w/w suspension of sodium hydride in mineral oil were added, whilst ice-cooling, to the resulting solution. The mixture was then stirred at room temperature for 30 minutes. 1.4 g of 1-[2-chloro-2-(2,4,6-trimethylphenyl)ethyl]imidazole dissolved in 7 ml of dry dimethylformamide was added to the solution, and the mixture was then heated at 60° to 65° C. for 20 hours. At the end of this time, the resulting mixture was treated and purified similarly to the procedure described in Example 1, to give 1.72 g of the title compound as an oil.

Infrared Absorption Spectrum (liquid film) $v_{max}$cm$^{-1}$: 1720, 1595, 1560, 1505.

Nuclear Magnetic Resonance Spectrum (CDCl$_3$) δ ppm: 1.93 (3H, singlet); 2.23 (3H, singlet); 2.58 (3H, singlet); 3.88 (3H, singlet); 4.43 (2H, doublet, J=7.0 Hz); 4.81 (1H, triplet, J=7.0 Hz); 6.54–7.36 (7H, multiplet); 7.86 (2H, doublet, J=8.0 Hz).

EXAMPLE 12

4-[1-(2,4,6-Trimethylphenyl)-2-(imidazol-1-yl)ethylthio]benzoic acid hydrochloride 1.68 g of methyl 4-[1-(2,4,6-trimethylphenyl)-2-(imidazol-1-yl)ethylthio]benzoate (prepared as described in Example 11) was dissolved in 18 ml of methanol. 18 ml of a 1N aqueous solution of sodium hydroxide were added to the resulting solution, and the mixture obtained was stirred at room temperature for 4.5 hours. The solvent was removed by distillation, and 9 ml of a 1N aqueous solution of sodium hydroxide were added to the residue. The resulting mixture was extracted with chloroform, and the aqueous layer was acidified (pH 2 to 3) with 6N aqueous hydrochloric acid. The crystals which precipitated were collected by filtration, washed with water and dried, followed by recrystallization from a mixture of ethanol and ethyl acetate, to give 1.22 g of the title compound as colorless crystals, melting at 235°–241° C.

Infrared Absorption Spectrum (KBr) $v_{max}$ cm$^{-1}$: 3380, 1710, 1595, 1570, 1545.

Nuclear Magnetic Resonance Spectrum [(CD$_3$)$_2$SO] δ ppm: 2.16 (6H, singlet); 2.59 (3H, singlet); 4.85 (2H, doublet, J=7.0 Hz); 5.13 (1H, triplet, J=7.0 Hz); 6.82 (1H, singlet); 6.92 (1H, singlet); 7.43 (2H, doublet, J=8.0 Hz); 7.56 (1H, singlet); 7.79 (1H, singlet); 7.82 (2H, doublet, J=8.0 Hz); 9.29 (1H, singlet).

EXAMPLE 13

Methyl 4-[1-(2-methoxyphenyl)-2-(imidazol-1-yl)ethylthio]benzoate 8.3 ml of trifluoroacetic acid were added, whilst ice-cooling, to a mixture of 578 mg of methyl 4-mercaptobenzoate and 500 mg of 1-[2-hydroxy-2-(2-methoxyphenyl)ethyl]imidazole, and the mixture was stirred at a temperature between 0° and 5° C. for 2.7 hours, and then at room temperature for 2.5 hours.

At the end of this time, the trifluoroacetic acid was removed by distillation under reduced pressure, and an aqueous solution of sodium bicarbonate was added to the residue. The resulting mixture was extracted with ethyl acetate, and then the extract was washed with a saturated aqueous solution of sodium chloride and dried over anhydrous magnesium sulfate. The solvent was removed by distillation under reduced pressure, and the residue was purified by silica gel column chromatography eluted with a 15:1 by volume mixture of ethyl acetate and methanol, to give 691 mg of the title compound as a colorless oil. This compound was identical with that obtained as described in Example 9 in its infrared absorption spectrum and nuclear magnetic resonance spectrum.

EXAMPLE 14

Methyl 4-[1-(2-methoxyphenyl)-2-(imidazol-1-yl)ethylthio]benzoate 685 mg of triphenylphosphine were added, at a temperature between 0° and 5° C., to a solution of 500 mg of diethyl azodicarboxylate in 6.17 ml of tetrahydrofuran, and the mixture was stirred for 20 minutes. A solution of 570 mg of 1-[2-hydroxy-2-(2-methoxyphenyl)ethyl]imidazole in 7 ml of tetrahydrofuran was added to the resulting solution at a temperature between $-10°$ and $-15°$ C., and the mixture was stirred for 20 minutes. A solution of 439 mg of methyl 4-mercaptobenzoate in 8.4 ml of tetrahydrofuran was added at the same temperature to the mixture, which was then stirred at between 0° and 5° C. for 30 minutes, and then at room temperature for 25 minutes. A saturated aqueous solution of sodium chloride was added, and the reaction mixture was extracted with ethyl acetate. The extract was washed with water and then dried over anhydrous magnesium sulfate. The solvent was removed by distillation, and the residue was purified by the same method as described in Example 13, to give 223 mg of the title compound. This compound was identical with that obtained as described in Example 9 in its infrared absorption spectrum and nuclear magnetic resonance spectrum.

EXAMPLE 15

Methyl 4-[1-(2-methylphenyl)-2-(imidazol-1-yl)ethylthio]benzoate 1.64 g of methyl 4-mercaptobenzoate was dissolved in 10.4 ml of dry dimethylformamide, and 424 mg of a 55% w/w suspension of sodium hydride in mineral oil were added, whilst ice-cooling. The resulting mixture was then stirred at room temperature for 30 minutes. 12 ml of dry dimethylformamide containing 2.15 g of 1-[2-chloro-2-(2-methylphenyl)ethyl]imidazole were added to the resulting solution, and the mixture was heated at a temperature between 60° and 70° C. for 5.5 hours. At the end of this time, the resulting solution was treated and purified by the same procedure as described in Example 1, to give 2.62 g of the title compound as an oil.

Infrared Absorption Spectrum (liquid film) $\nu_{max}$ cm$^{-1}$: 1715, 1595, 1560, 1505.

Nuclear Magnetic Resonance Spectrum (CDCl$_3$) $\delta$ ppm: 2.10 (3H, singlet); 3.87 (3H, singlet); 4.32 (1H, doublet, J=6.0 Hz); 4.32 (1H, doublet, J=7.0 Hz); 4.75 (1H, doublet of doublets, J=6.0 & 7.0 Hz); 6.56 (1H, singlet); 6.86 (1H, singlet); 6.92–7.46 (7H, multiplet); 7.86 (2H, doublet, J'8.0 Hz).

EXAMPLE 16

4-[1-(2-Methylphenyl)-2-(imidazol-1-yl)ethylthio]benzoic acid hydrochloride 28.8 ml of a 1N aqueous solution of sodium hydroxide were added to a solution of 2.54 g of methyl 4-[1-(2-methylphenyl)-2-(imidazol-1-yl)ethylthio]benzoate (prepared as described in Example 15) in 28.8 ml of methanol, and the resulting mixture was stirred at room temperature for 3 hours. The solvent was then removed by distillation under reduced pressure, and 14.4 ml of a 1N aqueous solution of sodium hydroxide were added to the residue. The resulting mixture was extracted with chloroform, and the aqueous layer was acidified with concentrated hydrochloric acid to a pH value of 2–3. The precipitated crystals were filtered, washed with water, dried and recrystallized from a mixture of ethanol and ethyl acete, to give 2.0 g of the title compound as colorless crystals, melting at 162°–166° C.

Infrared Absorption Spectrum (KBr) $\nu_{max}$ cm$^{-1}$: 3380, 1700, 1630, 1590.

Nuclear Magnetic Resonance Spectrum [(CD$_3$)$_2$SO] $\delta$ ppm: 2.39 (3H, singlet); 4.86 (1H, doublet, J=7.0 Hz); 4.88 (1H, doublet, J=7.0 Hz); 5.28 (1H, triplet, J=7.0 Hz); 7.14–7.97 (10H, multiplet); 9.37 (1H, singlet).

EXAMPLE 17

Methyl 4-[1-(2,4-dimethoxyphenyl)-2-(imidazol-1-yl)ethylthio]benzoate 10.9 ml of trifluoroacetic acid were added, whilst ice-cooling, to a mixture of 766 mg of methyl 4-mercaptobenzoate and 754 mg of 1-[2-hydroxy-2-(2,4-dimethoxyphenyl)ethyl]imidazole, and the resulting mixture was stirred at a temperature between 0° and 5° C. for 1.5 hours. The resulting solution was treated and purified according to the same procedure as described in Example 13, to give 495 mg of the title compound as a colorless oily substance.

Infrared Absorption Spectrum (liquid film) $\nu_{max}$ cm$^{-1}$: 1715, 1610, 1595, 1505.

Nuclear Magnetic Resonance Spectrum (CDCl$_3$) $\delta$ppm: 3.78 (6H, singlet); 3.88 (3H, singlet); 4.33 (2H, doublet, J=7.0 Hz); 5.01 (1H, triplet, J=7.0 Hz); 6.32–7.40 (8H, multiplet); 7.91 (2H, doublet, J=8.0 Hz).

EXAMPLE 18

4-[1-(2,4-Dimethoxyphenyl)-2-(imidazol-1-yl)ethylthio]benzoic acid hydrochloride 4.78 ml of a 1N aqueous solution of sodium hydroxide were added to a solution of 476 mg of methyl 4-[1-(2,4-dimethoxyphenyl)-2-(imidazol-1-yl)ethylthio]benzoate (prepared as described in Example 17) in 4.78 ml of methanol, and the resulting mixture was stirred overnight at room temperature. The mixture was then treated and purified by the same method as described in Example 10, to give 393 mg of the title compound as colorless crystals, melting at 176°–182° C.

Infrared Absorption Spectrum (KBr) $\nu_{max}$ cm$^{-1}$: 3420, 1700, 1610, 1590, 1545, 1505.

Nuclear Magnetic Resonance Spectrum [(CD$_3$)$_2$SO] δ ppm: 3.75 (3H, singlet); 3.80 (3H, singlet); 4.75 (2H, doublet, J=7.0 Hz); 5.26 (1H, triplet, J=7.0 Hz); 6.43–6.60 (2H, multiplet); 7.27–7.70 (5H, multiplet); 7.85 (2H, doublet, J=8.0 Hz); 9.08 (1H, singlet).

EXAMPLE 19

Methyl 4-[1-(2,4,6-trimethoxyphenyl)-2-(imidazol-1-yl)ethylthio]benzoate 13.5 ml of trifluoroacetic acid were added, whilst ice-cooling, to a mixture of 940 mg of methyl 4-mercaptobenzoate and 1.04 g of 1-[2-hydroxy-2-(2,4,6-trimethoxyphenyl)ethyl]imidazole, and the resulting mixture was stirred at a temperature between 0° and 5° C. for 2 hours. The reaction mixture was then treated and purified in a similar manner to that described in Example 13 to give 1.51 g of the title compound as a colorless oil.

Infrared Absorption Spectrum (liquid film) $\nu_{max}$ cm$^{-1}$: 1710, 1590, 1495.

Nuclear Magnetic Resonance Spectrum (CDCl$_3$) δ ppm: 3.78 (9H, singlet); 3.88 (3H, singlet); 4.46 (1H, doublet, J=7.0 Hz); 4.49 (1H, doublet, J=7.0 Hz); 5.14 (1H, triplet, J=7.0 Hz); 6.10 (2H, singlet); 6.76 (1H, singlet); 6.88 (1H, singlet); 7.28 (1H, singlet); 7.34 (2H, doublet, J=8.0 Hz); 7.92 (2H, doublet, J=8.0 Hz).

EXAMPLE 20

4-[1-(2,4,6-Trimethoxyphenyl)-2-(imidazol-1-yl)ethylthio]benzoic acid hydrochloride 13.9 ml of a 1N aqueous solution of sodium hydroxide were added to a solution of 1.49 g of methyl 4-[1-(2,4,6-trimethoxyphenyl)-2-(imidazol-1-yl)ethylthio]benzoate (prepared as described in Example 19) in 13.9 ml of methanol. The resulting mixture was stirred overnight at room temperature, and was then treated and purified in a similar manner to that described in Example 10, to give 809 mg of the title compound as colorless crystals, melting at 196°–200° C.

Infrared Absorption Spectrum (KBr) $\nu_{max}$ cm$^{-1}$: 3360, 1680, 1610, 1590, 1575.

Nuclear Magnetic Resonance Spectrum [(CD$_3$)$_2$SO] δ ppm: 3.78 (9H, singlet); 4.78 (2H, doublet, J=7.0 Hz); 5.30 (1H, triplet, J=7.0 Hz); 6.23 (2H, singlet); 7.44 (2H, doublet, J=8.0 Hz); 7.50 (1H, singlet); 7.58 (1H, singlet); 7.87 (2H, doublet, J=8.0 Hz); 9.08 (1H, singlet).

EXAMPLE 21

Methyl 4-[1-(2-chlorophenyl)-2-(imidazol-1-yl)ethylthio]benzoate 6.4 g of methyl 4-mercaptobenzoate were dissolved in 45 ml of dry dimethylformamide, and 1.7 g of a 55% w/w suspension of sodium hydride in mineral oil was added to the resulting solution, whilst ice-cooling. The resulting mixture was then stirred at room temperature for 30 minutes, after which a solution of 9.2 g of 1-[2-chloro-2-(2-chlorophenyl)ethyl]imidazole in 45 ml of dry dimethylformamide was added to the resulting solution, and the reaction mixture was heated at 50° C. for 6.5 hours. At the end of this time, the resulting solution was treated and purified in a similar manner to that described in Example 1, to give 8.08 g of the title compound as an oil.

Infrared Absorption Spectrum (liquid film) $\nu_{max}$ cm$^{-1}$: 1715, 1650, 1590, 1560, 1500.

Nuclear Magnetic Resonance Spectrum (CDCl$_3$) δ ppm: 3.87 (3H, singlet); 4.37 (2H, doublet, J=7.0 Hz); 5.21 (1H, triplet, J=7.0 Hz); 6.80 (1H, singlet); 6.99 (1H, singlet); 7.14–7.56 (7H, multiplet); 7.92 (2H, doublet, J=8.0 Hz).

EXAMPLE 22

4-[1-(2-Chlorophenyl)-2-(imidazol-1-yl)ethylthio]benzoic acid hydrochloride 43 ml of a 1N aqueous solution of sodium hydroxide were added to a solution of 4.01 g of methyl 4-[1-(2-chlorophenyl)-2-(imidazol-1-yl)ethylthio]benzoate (prepared as described in Example 21) in 43 ml of methanol, and the resulting mixture was stirred at room temperature for 3 hours. The reaction mixture was then treated and purified by the same method as described in Example 10, to give 3.57 g of the title compound as colorless crystals, melting at 210°–215° C.

Infrared Absorption Spectrum (KBr) $\nu_{max}$ cm$^{-1}$: 3430, 1705, 1690, 1635, 1595, 1580.

Nuclear Magnetic Resonance Spectrum [(CD$_3$)$_2$SO] δ ppm: 4.92 (2H, doublet, J=7.0 Hz); 5.48 (1H, triplet, J=7.0 Hz); 7.28–7.94 (10H, multiplet); 9.28 (1H, singlet).

EXAMPLE 23

Methyl 4-[1-cyclohexyl-2-(imidazol-1-yl)ethylthio]benzoate 779 mg of a 55% w/w suspension of sodium hydride in mineral oil were added to a solution of 3 g of methyl 4-mercaptobenzoate in 24 ml of dry dimethylformamide, and the resulting mixture was stirred at room temperature for 30 minutes. A solution of 3.8 g of 1-(2-chloro-2-cyclohexylethyl)imidazole in 36 ml of dry dimethylformamide was added to the resulting solution, and the reaction mixture was then heated at 60°–70° C. for 13.5 hours. At the end of this time, the resulting mixture was treated and purified by the same method as described in Example 1, to give 3.3 g of the title compound as an oil.

Infrared Absorption spectrum (liquid film) $\nu_{max}$ cm$^{-1}$: 1715, 1670, 1590, 1555, 1500.

Nuclear Magnetic Resonance Spectrum (CDCl$_3$) δ ppm: 0.95–2.05 (11H, multiplet); 3.30 (1H, triplet, J=7.0 Hz); 3.90 (3H, singlet); 3.95–4.40 (2H, multiplet); 6.85–7.65 (5H, multiplet); 7.92 (2H, doublet, J=8.0 Hz).

EXAMPLE 24

4-[1-Cyclohexyl-2-(imidazol-1-yl)ethylthio]benzoic acid hydrochloride 38.1 ml of a 1N aqueous solution of sodium hydroxide were added to 3.28 g of methyl 4-[1-cyclohexyl-2-(imidazol-1-yl)ethylthio]benzoate (prepared as described in Example 23) in 38.1 ml of methanol, and the resulting mixture was stirred at room temperature for 4 hours. The reaction mixture was then treated and purified by the same method as described in Example 10, to give 2.0 g of the title compound as colorless crystals, melting at 218°–222° C.

Infrared Absorption Spectrum (KBr) $\nu_{max}$cm$^{-1}$: 3430, 1710, 1595, 1565, 1540.

Nuclear Magnetic Resonance Spectrum (CDCl$_3$) δ ppm: 0.95–2.10 (11H, multiplet); 3.65–4.70 (3H, multiplet); 7.27 (2H, doublet, J=8.0 Hz); 7.35 (1H, singlet); 7.76 (1H, singlet); 7.84 (2H, doublet, J=8.0 Hz); 9.36 (1H, singlet).

EXAMPLE 25

Methyl 4-[1-(2,6-dimethoxyphenyl)-2-(imidazol-1-yl)ethylthio]benzoate 20 ml of trifluoroacetic acid were added, whilst ice-cooling, to a mixture of 1.38 g of methyl 4-mercaptobenzoate and 1.36 g of 1-[2-hydroxy-2-(2,6-dimethoxyphenyl)ethyl]imidazole, and the resulting mixture was stirred at a temperature between 0° and 5° C. for 2 hours. The reaction mixture was then treated and purified by the same method as described in Example 13, to give 2.02 g of the title compound as a colorless oil.

Infrared Absorption Spectrum (liquid film) $\nu_{max}$cm$^{-1}$: 1720, 1600, 1565, 1510.

Nuclear Magnetic Resonance Spectrum (CDCl$_3$) δ ppm: 3.90 (3H, singlet); 5.52 (2H, doublet, J=7.0 Hz); 5.23 (1H, triplet, J=7.0 Hz); 6.45–7.46 (8H, multiplet); 7.92 (2H, doublet, J=8.0 Hz).

EXAMPLE 26

4-[1-(2,6-Dimethoxyphenyl)-2-imidazol-1-yl)ethylthio]benzoic acid hydrochloride 20 ml of a 1N aqueous solution of sodium hydroxide were added to a solution of 2.0 g of methyl 4-[1-(2,6-dimethoxyphenyl)-2-(imidazol-1-yl)ethylthio]benzoate (prepared as described in Example 25) in 20 ml of methanol, and the reaction mixture was stirred at room temperature for 3 hours. The resulting mixture was then treated and purified by the same procedure as described in Example 10, to give 1.71 g of the title compound as colorless crystals, melting at 213°–217° C.

Infrared Absorption Spectrum (KBr) $\nu_{max}$cm$^{-1}$: 3400, 1700, 1595, 1545.

Nuclear Magnetic Resonance Spectrum [(CD$_3$)$_2$SO]δ ppm: 4.86 (2H, doublet, J=7.0 Hz); 5.39 (1H, triplet, J=7.0 Hz); 6.68 (2H, doublet, J=8.0 Hz); 7.28 (1H, triplet, J=8.0 Hz); 7.46 (2H, doublet, J=8.0 Hz); 7.52 (1H, singlet); 7.60 (1H, singlet); 7.91 (2H, doublet, J=8.0 Hz); 9.12 (1H, singlet).

EXAMPLE 27

Methyl 4-[1-(3,4,5-trimethoxyphenyl)-2-(imidazol-1-yl)ethylthio]benzoate 48.5 mg of a 55% w/w suspension of sodium hydride in mineral oil were added, whilst ice-cooling, to a solution of 187 mg of methyl 4-mercaptobenzoate in 1.3 ml of dry dimethylformamide, and the reaction mixture was then stirred at room temperature for 30 minutes. To this solution was added 1.3 ml of dry dimethylformamide containing 330 mg of 1-[2-chloro-2-(3,4,5-trimethoxyphenyl)ethyl]imidazole, and the reaction mixture was heated at 60°–70° C. for 7.5 hours. At the end of this time, the resulting mixture was treated and purified by the same method as described in Example 1, to give 187.7 mg of the title compound as an oil.

Infrared Absorption Spectrum (liquid film) $\nu_{max}$cm$^{-1}$: 1710, 1595, 1560, 1505.

Nuclear Magnetic Resonance Spectrum (CDCl$_3$) δ ppm: 3.78 (6H, singlet); 3.82 (3H, singlet); 3.79 (3H, singlet); 4.22–4.53 (3H, multiplet); 6.42 (2H, singlet); 6.72 (1H, singlet); 7.00 (1H, singlet); 7.28 (1H, snglet); 7.36 (2H, doublet, J=8.0 Hz); 7.96 (2H, doublet, J=8.0 Hz).

EXAMPLE 28

4-[1-(3,4,5-Trimethoxyphenyl)-2-(imidazol-1-yl)ethylthio]benzoic acid 1.6 ml of a 1N aqueous solution of sodium hydroxide was added to a solution of 170.6 mg of methyl 4-[1-(3,4,5-trimethoxyphenyl)-2-(imidazol-1-yl)ethylthio]benzoate (prepared as described in Example 27) in 1.6 ml of methanol, and the reaction mixture was stirred at room temperature for 2 hours. The solvent was then removed by distillation under reduced pressure, and 0.8 ml of a 1N aqueous solution of sodium hydroxide was added to the residue. The resulting mixture was extracted with chloroform, and the aqueous layer was adjusted to a pH value of 6.0 using concentrated hydrochloric acid and then extracted with chloroform. The chloroform extract was washed with a concentrated aqueous solution of sodium chloride and dried. The solvent was removed by distillation under reduced pressure, to give 91.4 mg of the title compound as a powdery substance, melting at 94°–97° C.

Infrared Absorption Spectrum (KBr) $\nu_{max}$cm$^{-1}$: 3420, 1700, 1595, 1560, 1510.

Nuclear Magnetic Resonance Spectrum [(CD$_3$)$_2$SO] δ ppm: 4.50 (2H, doublet, J=7.0 Hz); 5.02 (1H, triplet, J=7.0 Hz); 6.70 (2H, singlet); 6.83 (1H, singlet); 7.14 (1H, singlet); 7.46 (2H, doublet, J=8.0 Hz); 7.52 (1H, singlet); 7.86 (2H, doublet, J=8.0 Hz).

EXAMPLE 29

Methyl 4-[1-(3-methoxyphenyl)-2-(imidazol-1-yl)ethylthio]benzoate 144 mg of a 55% w/w suspension of sodium hydride in mineral oil were added, whilst ice-cooling, to a solution of 555 mg of methyl 4-mercaptobenzoate in 4 ml of dry dimethylformamide, and the resulting mixture was stirred at room temperature for 30 minutes. A solution of 710 of 1-[2-chloro-2-(3-methoxyphenyl)ethyl]imidazole in 3 ml of dry dimethylformamide was added to this solution, and the reaction mixture was heated at 60°–70° C. for 5.5 hours. At the end of this time, the resulting mixture was treated and purified according to the same procedure as described in Example 1, to give 631 mg of the title compound as an oil.

Infrared Absorption Spectrum (liquid film) $\nu_{max}$cm$^{-1}$: 1720, 1675, 1595, 1290.

Nuclear Magnetic Resonance Spectrum (CDCl$_3$) δ ppm: 3.77 (3H, singlet); 3.90 (3H, singlet); 4.22–4.75 (3H, multiplet); 6.69–7.56 (9H, multiplet); 7.95 (2H, doublet, J=8.0 Hz).

EXAMPLE 30

4-[1-(3-Methoxyphenyl)-2-(imidazol-1-yl)ethylthio]benzoid acid 3.18 ml of a 1N aqueous solution of sodium hydroxide were added to a solution of 585 mg of methyl 4-[1-(3-methoxyphenyl)-2-(imidazol-1-yl)ethylthio]benzoate (prepared as described in Example 29) in 6 ml of methanol, and the resulting mixture was stirred at room temperature for 5.5 hours. The reaction mixture was then treated and purified according to the same method as described in Example 28, to give 390 mg of the title compound as a powder, melting at 75°–77° C.

Infrared Absorption Spectrum (KBr) $\nu_{max}$cm$^{-1}$: 3410, 1695, 1590, 1260.

Nuclear Magnetic Resonance Spectrum [(CD$_3$)$_2$SO] δ ppm: 3.73 (3H, singlet); 4.50 (2H, doublet, J=7.0 Hz); 5.04 (1H, triplet, J=7.0 Hz); 6.62–7.67 (9H, multiplet); 7.85 (2H, doublet, J=8.0 Hz).

EXAMPLE 31

Methyl 4-[3-(4-chlorophenyl)-1-(imidazol-1-ylmethyl)propylthio]benzoate 11 mg of a 55% w/w suspension of sodium hydride in mineral oil were added, whilst ice-cooling, to a solution of 40 mg of methyl 4-mercaptobenzoate in 0.25 ml of dry dimethylformamide, and the resulting mixture was stirred at room temperature for 30 minutes. A solution of 52 mg of 1-[4-(4-chlorophenyl)-2-chlorobutyl]imidazole in 0.25 ml of dry dimethylformamide was added to this solution, and the resulting mixture was heated at 60°–70° C. for 5 hours. At the end of this time, the reaction mixture was treated and purified according to the same method as described in Example 1, to give 34 mg of the title compound as an oil.

Infrared Absorption Spectrum (liquid film) $\nu_{max}$cm$^{-1}$: 1715, 1670, 1595, 1560, 1490.

Nuclear Magnetic Resonance Spectrum (CDCl$_3$) δ ppm: 1.55–2.05 (2H, multiplet); 2.40–3.00 (2H, multiplet); 3.12–3.60 (1H, multiplet); 3.89 (3H, singlet); 4.05 (2H, doublet, J=7.0 Hz); 6.76–7.65 (9H, multiplet); 7.95 (2H, doublet, J=8.0 Hz).

EXAMPLE 32

Sodium 4-[3-(4-chlorophenyl)-1-(imidazol-1-ylmethyl)propylthio]benzoate

360 μl of a 1N aqueous solution of sodium hydroxide were added to a solution of 34 mg of methyl 4-[3-(4-chlorophenyl)-1-(imidazol-1-ylmethyl)propylthio]benzoate (prepared as described in Example 31) in 360 μl of methanol, and the resulting mixture was stirred at room temperature for 3 hours. The reaction mixture was then treated and purified by the same method as described in Example 8, to give 21 mg of the title compound as a colorless powder.

Infrared Absorption Spectrum (KBr) $\nu_{max}$cm$^{-1}$: 3400, 1595, 1550, 1505.

Nuclear Magnetic Resonance Spectrum [(CD$_3$)$_2$SO] δ ppm: 1.51–1.98 (2H, multiplet); 2.60–2.96 (2H, multiplet); 3.15–3.70 (1H, multiplet); 4.20 (2H, doublet, J=7.0 Hz); 6.90 (1H, singlet); 7.08–7.43 (7H, multiplet); 7.68 (1H, singlet); 7.88 (2H, doublet, J=8.0 Hz).

EXAMPLE 33

Methyl 4-[1-(2-hydroxyphenyl)-2-(imidazol-1-yl)ethylthio]benzoate

814 μl of a 1M aqueous solution of boron tribromide in methylene chloride were added to a solution of 300 mg of methyl 4-[1-(2-methoxyphenyl)-2-(imidazol-1-yl)ethylthio]benzoate (prepared as described in Example 9) in 1.2 ml of methylene chloride at −78° C., and the resulting mixture was allowed to react at room temperature for 5 hours, and then poured into ice-water and stirred for 30 minutes. At the end of this time, the reaction mixture was neutralized with an aqueous solution of sodium bicarbonate, and then extracted with chloroform. The extract was washed with an aqueous solution of sodium chloride and dried over anhydrous sodium sulfate. The solvent was removed by distillation and the residue was purified by silica gel column chromatography eluted with a 30:1 by volume mixture of chloroform and methanol, to give 25 mg of the title compound as an oil.

Infrared Absorption Spectrum (liquid film) $\nu_{max}$cm$^{-1}$: 1710, 1590, 1555, 1505.

Nuclear Magnetic Resonance Spectrum (CDCl$_3$) δ ppm: 3.88 (3H, singlet); 4.42 (2H, doublet, J=7.0 Hz); 6.60–7.55 (9H, multiplet); 7.90 (2H, doublet, J=8.0 Hz).

EXAMPLE 34

4-[1-(2-Hydroxyphenyl)-2-(imidazol-1-yl)ethylthio]benzoic acid

694 μl of a 1N aqueous solution of sodium hydroxide were added to a solution of 61.5 mg of methyl 4-[1-(2-hydroxyphenyl)-2-(imidazol-1-yl)ethylthio]benzoate (prepared as described in Example 33) in 694 μl of methanol, and the resulting mixture was stirred at room temperature for 3 hours. The reaction mixture was then neutralized with 694 μl of a 1N aqueous solution of hydrochloric acid, and methanol was removed by distillation under reduced pressure. The remaining solution was subjected to chromatography through a Lobar column (Lichroprep, trade mark, RP-8, size B, produced by Merck) to give 32.2 mg of the title compound as a powdery substance, melting at 186°–190° C., from the fraction eluted with 30% v/v aqueous methanol.

Infrared Absorption Spectrum (KBr) $\nu_{max}$cm$^{-1}$: 3350, 1590, 1540, 1510.

Nuclear Magnetic Resonance Spectrum [(CD$_3$)$_2$SO] δ ppm: 4.42 (1H, doublet, J=7.0 Hz); 4.51 (1H, doublet, J=7.0 Hz); 5.06 (1H, triplet, J=7.0 Hz); 6.68–7.50 (9H, multiplet); 7.81 (2H, doublet, J=8.0 Hz).

EXAMPLE 35

Methyl 4-[1-(4-trifluoromethylphenyl)-2-(imidazol-1-yl)ethylthio]benzoate 292 mg of a 55% w/w suspension of sodium hydride in mineral oil were added to 1.13 g of methyl 4-mercaptobenzoate in 8 ml of dry dimethylformamide, whilst ice-cooling, and the resulting mixture was stirred at room temperature for 30 minutes. 1.61 g of 1-[2-chloro-2-(4-trifluoromethylphenyl)ethyl]imidazole in 7 ml of dry dimethylformamide was added to this solution and the resulting mixture was heated at 60°–70° C. for 6 hours. At the end of this time, the reaction mixture was treated and purified by the same method as described in Example 1, to give 844 mg of the title compound as an oil.

Infrared Absorption Spectrum (liquid film) $\nu_{max}$cm$^{-1}$: 1710, 1660, 1615, 1590, 1540, 1510.

Nuclear Magnetic Resonance Spectrum (CDCl$_3$) δ ppm: 3.88 (3H, singlet); 4.24–4.72 (3H, multiplet); 6.66 (1H, singlet); 6.94 (1H, singlet); 7.07–7.68 (7H, multiplet); 7.90 (2H, doublet, J=8.0 Hz).

EXAMPLE 36

4-[1-(4-Trifluoromethylphenyl)-2-(imidazol-1-yl)ethylthio]benzoic acid 8 ml of a 1N aqueous solution of sodium hydroxide were added to 792 mg of methyl 4-[1-(4-trifluoromethylphenyl)-2-(imidazol-1-yl)ethylthio]benzoate (prepared as described in Example 35) in 8 ml of methanol, and the resulting mixture was stirred at room temperature for 4 hours. The reaction mixture was then treated and purified by the same method as described in Example 28, to give 481 mg of the title compound as a powder, melting at 92°–95° C.

Infrared Absorption Spectrum (KBr) $\nu_{max}$cm$^{-1}$: 3400, 1700, 1620, 1590, 1560, 1510.

Nuclear Magnetic Resonance Spectrum [(CD$_3$)$_2$SO] δ ppm: 4.41 (1H, doublet, J=6.0 Hz); 4.41 (1H, doublet J=7.0 Hz); 4.65 (1H, doublet of doublets, J=6.0 & 7.0 Hz); 6.71 (1H, singlet); 7.05 (1H, singlet); 7.26–7.76 (7H, multiplet); 7.98 (2H, doublet, J=8.0 Hz).

EXAMPLE 37

Methyl 4-[1-(2-trifluoromethylphenyl)-2-(imidazol-1-yl)ethylthio]benzoate 374 mg of a 55% w/w suspension of sodium hydride in mineral oil were added to 1.44 g of methyl 4-mercaptobenzoate in 9.1 mg of dry dimethylformamide, whilst ice-cooling, and the resulting mixture was stirred at room temperature for 30 minutes. 2.14 g of 1-[2-chloro-2-(2-trifluoromethylphenyl)ethyl]imidazole in 11.2 ml of dry dimethylformamide were added to this solution, and the resulting mixture were heated at 60°–70° C. for 6 hours. At the end of this time, the reaction mixture was treated and purified by the same method as described in Example 1, to give 2.34 g of the title compound as white cyrstals, melting at 121°–126° C.

Infrared Absorption Spectrum (Nujol) $\nu_{max}$cm$^{-1}$: 1715, 1645, 1630, 1595, 1560, 1505.

Nuclear Magnetic Resonance Spectrum (CDCl$_3$) δ ppm: 3.88 (3H, singlet); 4.33 (1H, doublet, J=7.0 Hz); 4.38 (1H, doublet, J=6.0 Hz); 4.51 (1H, doublet of doublets, J=7.0 & 6.0 Hz); 6.78 (1H, singlet); 6.98 (1H, singlet); 7.15–7.80 (7H, multiplet); 7.90 (2H, doublet, J=8.0 Hz).

EXAMPLE 38

4-[1-(2-Trifluoromethylphenyl)-2-(imidazol-1-yl)ethylthio]benzoic acid hydrochloride 17.6 of 1N aqueous solution of sodium hydroxide were added to 1.79 g of methyl 4-[1-(2-trifluoromethylphenyl)-2-(imidazol-1-yl)ethylthio]benzoate (prepared as described in Example 37) in 17.6 ml of methanol, and the resulting mixture was stirred at room temperature for 4.5 hours. 8.8 ml of a 1N aqueous solution of sodium hydroxide were added to the reaction mixture and it was then neutralized with 1N aqueous hydrochloric acid, after which it was treated and purified by the same method as described in Example 16, to give 1.61 g of the title compound as colorless crystals, melting at 198°–202° C.

Infrared Absorption Spectrum (KBr) $\nu_{max}$cm$^{-1}$: 1680, 1585, 1560, 1530.

Nuclear Magnetic Resonance Spectrum [(CD$_3$)$_2$SO] δ ppm: 4.75–5.23 (3H, multiplet); 7.30–8.20 (10H, multiplet); 9.33 (1H, singlet).

EXAMPLE 39

Methyl 4-[1-(2-methoxyphenyl)-2-(imidazol-1-yl)ethylsulfinyl]benzoate 5 ml of dry methylene chloride containing 304 mg of 3-chloroperbenzoic acid were added to 368 mg of methyl 4-[1-(2-methoxyphenyl)-2-(imidazol-1-yl)ethylthio]benzoate (prepared as described in Example 9) in 7 ml of dry methylene chloride, and the resulting mixture was stirred at 0°–5° C. for 30 minutes. At the end of this time, chloroform was added to the reaction mixture, and the resulting mixture was washed with a saturated aqueous solution of sodium chloride and dried over anhydrous magnesium sulfate. The solvent was removed by distillation under reduced pressure, and the residue was purified by silica gel column chromatography eluted with a 10:1 volume mixture of ethyl acetate and methanol, to give 263 mg of the title compound as colorless crystals, melting at 113°–115° C.

Infrared Absorption Spectrum (KBr) $\nu_{max}$cm$^{-1}$: 1720, 1600, 1495, 1276, 1250.

Nuclear Magnetic Resonance Spectrum (CDCl$_3$) δ ppm: 3.53 (3H, singlet); 3.92 (3H, singlet); 4.20–4.93 (3H, multiplet); 6.60–7.55 (9H, multiplet); 8.00 (2H, doublet, J=8.0 Hz).

EXAMPLE 40

4-[1-(2-Methoxyphenyl)-2-(imidazol-1-yl)ethylsulfinyl]benzoic acid 1.22 ml of a 1N aqueous solution of sodium hydroxide was added to a solution of 235 mg of methyl 4-[1-(2-methoxyphenyl)-2-(imidazol-1-yl)ethylsulfinyl]benzoate (prepared as described in Example 39) in 3 ml of methanol, and the resulting mixture was stirred at room temperature for 7 hours. The reaction mixture was then neutralized with 1.22 ml of 1N aqueous hydrochloric acid, and then treated and purified by the same method as described in Example 34, to give 155 mg of the title compound as a colorless powdery substance, melting at 157°–159° C.

Infrared Absorption Spectrum (KBr) $\nu_{max}$cm$^{-1}$: 3400, 1700, 1596, 1495, 1250.

Nuclear Magnetic Resonance Spectrum [(CD$_3$)$_2$SO] δ ppm: 3.50 (3H, singlet); 4.03–5.10 (4H, multiplet); 6.62–7.60 (9H, multiplet); 7.97 (2H, doublet, J=8.0 Hz).

EXAMPLE 41

Methyl 4-[1-(2-methoxyphenyl)-2-(imidazol-1-yl)ethylsulfonyl]benzoate 609 mg of 3-chloroperbenzoic acid in 10 ml of dry methylene chloride were added to 368 mg of methyl 4-[1-(2-methoxyphenyl)-2-(imidazol-1-yl)ethylthio]benzoate (prepared as described in Example 9) in 7 ml of dry methylene chloride, whilst ice-cooling, and the resulting mixture was stirred at room temperature for 2 hours. The reaction mixture was then treated and purified by the same method as described in Example 39, to give 278 mg of the title compound as colorless crystals, melting at 150°–151° C.

Infrared Absorption Spectrum (KBr) $\nu_{max}$cm$^{-1}$: 1730, 1600, 1497, 1286.

Nuclear Magnetic Resonance Spectrum (CDCl$_3$) δ ppm: 3.29 (3H, singlet); 3.95 (3H, singlet); 4.30–5.45

(3H, multiplet); 6.42–7.78 (9H, multiplet); 8.03 (2H, doublet, J=8.0 Hz).

EXAMPLE 42

4-[1-(2-Methoxyphenyl)-2-(imidazol-1-yl)ethylsulfonyl]benzoic acid 1.30 ml of a 1N aqueous solution of sodium hydroxide was added to 260 mg of methyl 4-[1-(2-methoxyphenyl)-2-(imidazol-1-yl)ethylsulfonyl]benzoate (prepared as described in Example 41) in 4 ml of methanol, and the resulting mixture was stirred at room temperature for 1.5 hours. At the end of this time, the resulting mixture was neutralized with 1.30 ml of 1N aqueous hydrochloric acid, and the reaction mixture was treated and purified by the same method as described in Example 34, to give 214 mg of the title compound as a colorless powdery substance, melting at 134°–138° C.

Infrared Absorption Spectrum (KBr) $\nu_{max}$cm$^{-1}$: 3370, 1600, 1565, 1500, 1370.

Nuclear Magnetic Resonance Spectrum [(CD$_3$)$_2$SO] δ ppm: 3.26 (3H, singlet); 4.90 (2H, doublet, J=7.0 Hz); 5.44 (1H, triplet, J=7.0 Hz); 6.60–7.77 (9H, multiplet); 8.02 (2H, doublet, J=8.0 Hz).

EXAMPLE 43

Methyl 4-[2-(2-methoxyphenyl)-1-(imidazol-1-yl)propylthio]-benzoate 5.2 ml of trifluoroacetic acid were added, whilst ice-cooling, to a mixture of 363 mg of methyl 4-mercaptobenzoate and 334 mg of 1-[2-hydroxy-2-(2-methoxyphenyl)propyl]imidazole, and the resulting mixture was stirred at 0°–5° C. for 2.5 hours. The reaction mixture was then treated and purified by the same method as described in Example 13, to give 482 mg of the title compound as a colorless oily substance.

Infrared Absorption Spectrum (liquid film) $\nu_{max}$cm$^{-1}$: 1715, 1595, 1580, 1540, 1500.

Nuclear Magnetic Resonance Spectrum (CDCl$_3$) δ ppm: 1.48 (3H, singlet); 3.90 (3H, singlet); 4.00 (3H, singlet); 4.30 (1H, doublet, J=14.0 Hz); 5.19 (1H, doublet, J=14.0 Hz); 6.56 (1H, singlet); 6.76–7.55 (8H, multiplet); 7.85 (2H, doublet, J=8.0 Hz).

EXAMPLE 44

4-[2-(2-Methoxyphenyl)-1-(imidazol-1-yl)propylthio]-benzoic acid 4.7 ml of a 1N aqueous solution of sodium hydroxide were added to 450 mg of methyl 4-[2-(2-methoxyphenyl)-1-(imidazol-1-yl)propylthio]benzoate prepared as described in Example 43) in 4.7 ml of methanol, and the resulting mixture was stirred at room temperature for 3 hours. The reaction mixture was then treated and purified by the same method as described in Example 28, to give 300 mg of the title compound as a powder, melting at 118°–124° C.

Infrared Absorption Spectrum (Nujol) $\nu_{max}$cm$^{-1}$: 1690, 1590, 1550, 1530, 1500.

Nuclear Magnetic Resonance Spectrum (CDCl$_3$) δ ppm: 1.48 (3H, singlet); 3.95 (3H, singlet); 4.35 (1H, doublet, J=14.0 Hz); 5.25 (1H, doublet, J=14.0 Hz); 6.45–8.20 (11H, multiplet).

EXAMPLE 45

Methyl 4-[1-(3-pyridyl)-2-(imidazol-1-yl)ethylthio]-benzoate 192 mg of a 55% w/w suspension of sodium hydride in mineral oil were added to 4 ml of dry dimethylformamide containing 740 mg of methyl 4-mercaptobenzoate, whilst ice-cooling, and the resulting mixture was stirred at room temperature for 30 minutes. 830 mg of 1-[2-chloro-2-(3-pyridyl)ethyl]imidazole in 4 ml of dry dimethylformamide were added to the reaction mixture, and the resulting mixture was heated at 60°–70° C. for 5 hours. At the end of this time the reaction mixture was treated and purified by the same method as described in Example 1, to give 615 mg of the title compound as an oil.

Infrared Absorption Spectrum (liquid film) $\nu_{max}$cm$^{-1}$: 1710, 1655, 1590, 1490, 1280.

Nuclear Magnetic Resonance Spectrum (CDCl$_3$) δ ppm: 3.90 (3H, singlet); 4.18–4.80 (3H, multiplet); 6.65–8.80 (11H, multiplet).

EXAMPLE 46

4-[1-(3-Pyridyl)-2-(imidazol-1-yl)ethylthio]benzoic acid 3.39 ml of a 1N aqueous solution of sodium hydroxide were added to 575 mg of methyl-4-[1-(3-pyridyl)-2-(imidazol-1-yl)ethylthio]benzoate (prepared as described in Example 45) in 7 ml of methanol, and the resulting mixture was stirred at 40° C. for 5 hours. At the end of this time, the resulting mixture was neutralized with 3.39 ml of 1N aqueous hydrochloric acid, and the reaction mixture was treated and purified by the same method as described in Example 34, to give 305 mg of the title compound as a powder, melting at 80°–83° C.

Infrared Absorption Spectrum (Nujol) $\nu_{max}$cm$^{-1}$: 1690, 1590.

Nuclear Magnetic Resonance Spectrum [(CD$_3$)$_2$SO] δ ppm: 4.53 (2H, doublet, J=7.0 Hz); 5.06 (1H, triplet, J=7.0 Hz); 6.25–8.65 (11H, multiplet).

EXAMPLE 47

Methyl 4-[1-(2-furyl)-2-(1-imidazolyl)ethylthio]benzoate 3.5 g of methyl 4-mercaptobenzoate and 2.5 g of 1-[2-hydroxy-2-(2-furyl)ethyl]imidazole were mixed, and 50.7 ml of trifluoroacetic acid were added, whilst ice-cooling, to the resulting mixture. The mixture was stirred at between 0° and 5° C. for 1 hour. At the end of this time, the reaction mixture was treated and purified similarly to the procedure described in Example 13, to yield 2.96 g of the title compound as a colorless oil.

Infrared Absorption Spectrum (liquid film) $\nu_{max}$cm$^{-1}$: 1720, 1595, 1560, 1505.

Nuclear Magnetic Resonance Spectrum (CDCl$_3$) δ ppm: 3.90 (3H, singlet); 4.22–4.74 (3H, multiplet); 6.05–6.37 (2H, multiplet); 6.72 (1H, singlet); 6.98 (1H, singlet); 7.24–7.48 (4H, multiplet); 7.96 (2H, doublet, J=8.0 Hz).

EXAMPLE 48

4-[1-(2-Furyl)-2-(1-imidazolyl)ethylthio]benzoic acid hydrochloride 2.94 g of 4-[1-(2-furyl)-2-(1-imidazolyl)ethylthio]benzoic acid (prepared as described in Example 47) were dissolved in 35.8 ml of methanol, and 35.8 ml of a 1N aqueous solution of sodium hydroxide were added thereto. The mixture was stirred at room temperature for 3.5 hours. At the end of this time, the reaction mixture was treated and purified similarly to the procedure described in Example 10, to yield 2.74 g of the title compound as colorless crystals, melting at 80°–83° C.

infrared Absorption Spectrum (KBr) $\nu_{max}$cm$^{-1}$: 3380, 1695, 1590, 1570, 1545.

Nuclear Magnetic Resonance Spectrum [(CD$_3$)$_2$SO] δ ppm: 4.78 (2H, doublet, J=7.0 Hz); 5.26 (1H, triplet, J=7.0 Hz); 6.33 (2H, singlet); 7.15–7.70 (5H, multiplet); 7.95 (2H, doublet, J=8.0 Hz); 9.33 (1H, singlet).

We claim:

1. A compound of formula (I):

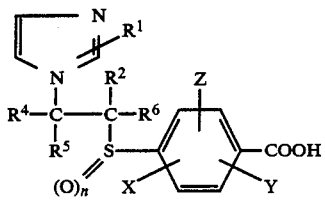

wherein:

$R^1$ represents a hydrogen atom or a methyl group;

$R^2$ represents a hydrogen atom, a $C_1$–$C_6$ alkyl group, a $C_2$–$C_6$ alkenyl group, a $C_2$–$C_6$ alkynyl group, a $C_3$–$C_8$ cycloalkyl group, a $C_3$–$C_8$ cycloalkyl group having at least one substituent selected from $C_1$–$C_6$ alkyl groups, an aryl group, a heterocyclic group or a carboxy group, or one of said alkyl, alkenyl and alkynyl groups having at least one substituent selected from the group consisting of:

(a) $C_1$–$C_4$ alkoxy groups, $C_1$–$C_6$ alkanoyloxy groups, $C_1$–$C_6$ alkanoyl groups, carboxy groups, $C_2$–$C_7$ alkoxycarbonyl groups, $C_2$–$C_7$ alkoxycarbonyloxy groups, carbamoyloxy groups, alkylcarbamoyloxy groups in which the alkyl part is $C_1$–$C_4$ alkyl, dialkylcarbamoyloxy groups in which each alkyl part is $C_1$–$C_4$ alkyl, carbamoyl groups, alkylcarbamoyl groups in which the alkyl part is $C_1$–$C_4$ alkyl, dialkylcarbamoyl groups in which each alkyl part is $C_1$–$C_4$ alkyl, hydroxy groups, carboxylic acylamino groups, $C_1$–$C_6$ alkylthio groups, nitro groups, cyano groups, amino groups, $C_1$–$C_6$ haloalkyl groups, halogen atoms, $C_1$–$C_6$ alkylsulfinyl groups, $C_1$–$C_6$ alkylsulfonyl groups, aryl groups, heterocyclic groups, $C_3$–$C_8$ cycloalkyl groups, and $C_3$–$C_8$ cycloalkyl groups having at least one substituent selected from $C_1$–$C_6$ alkyl groups;

$R^4$ represents a hydrogen atom, a $C_1$–$C_6$ alkyl group, a $C_2$–$C_6$ alkenyl group, a $C_2$–$C_6$ alkynyl group, an aryl group or an aromatic heterocyclic group, or said alkyl, alkenyl or alkynyl group having at least one substituent selected from the group consisting of:

$C_1$–$C_6$ alkoxy groups, $C_1$–$C_6$ haloalkyl groups, halogen atoms, aryl groups and aromatic heterocyclic groups;

$R^5$ and $R^6$ are independently selected from the group consisting of hydrogen atoms, $C_1$–$C_6$ alkyl groups, $C_2$–$C_6$ alkenyl groups and $C_2$–$C_6$ alkynyl groups;

X, Y and Z are independently selected from the group consisting of hydrogen atoms, $C_1$–$C_6$ alkyl groups, $C_1$–$C_6$ alkoxy groups, $C_1$–$C_6$ alkanoyloxy groups, hydroxy groups, $C_1$–$C_6$ alkylthio groups, cyano groups, amino groups, halogen atoms, $C_1$–$C_6$ alkylsulfinyl groups and $C_1$–$C_6$ alkylsulfonyl groups;

n is 0, 1 or 2 said aryl groups are $C_6$–$C_{14}$ carbocyclic aryl groups which are unsubstituted or have at least one substituent selected from the group consisting of $C_1$–$C_6$ alkyl groups and substituents (a) other than said aryl groups; and said aromatic heterocyclic groups are selected from the group consisting of 2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl;

said heterocyclic groups are selected from the group consisting of 2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl; and 2-tetrahydrofuryl, 2-tetrahydropyranyl, 2-pyrrolidinyl, 1-pyrrolidinyl, piperidino, 2-piperidyl, 3-piperidyl, 4-piperidyl, 4-thiazolidinyl, 1-piperazinyl, 4-acetyl-1-piperazinyl, 4-formyl-1-piperazinyl, morpholino and thiomorpholino;

said heterocyclic groups and said aromatic heterocyclic groups being unsubstituted or having at least one substituent selected from the group consisting of $C_1$–$C_6$ alkyl groups and substituents (a) other than said heterocyclic groups;

provided that when both $R^2$ and $R^6$ are individually selected from the group consisting of hydrogen and alkyl, then at least one of $R^4$ and $R^5$ is not selected from the group consisting of hydrogen, unsubstituted alkyl and unsubstituted alkenyl;

or a pharmaceutically acceptable ester, amide or salt thereof.

2. The compound as claimed in claim 1, wherein $R^2$, $R^4$, $R^5$ and $R^6$ are as defined in claim 1, provided that they are not all selected from the group consisting of hydrogen atoms and unsubstituted alkyl, alkenyl and alkynyl groups.

3. A compound of formula (I):

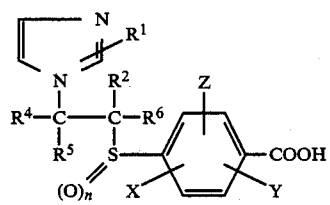

wherein:

$R^1$ represents a hydrogen atom or a methyl group;

$R^2$ represents a hydrogen atom, a $C_1$–$C_6$ alkyl group, a $C_2$–$C_6$ alkenyl group, a $C_2$–$C_6$ alkynyl group, a $C_3$–$C_6$ cycloalkyl group, an aryl group or an aromatic heterocyclic group, one of said alkyl, alkenyl or alkynyl groups being unsubstituted or having at least one substituent selected from the group consisting of substituents (a'):

(a') $C_1$–$C_6$ alkoxy groups, $C_1$–$C_6$ alkanoyloxy groups, hydroxy groups, $C_1$–$C_6$ alkylthio groups, cyano groups, trifluoromethyl groups, halogen atoms, $C_1$–$C_6$ alkylsulfinyl groups, $C_1$–$C_6$ alkylsulfonyl groups, aryl groups and aromatic heterocyclic groups, or said cycloalkyl group having at least one substituent selected from $C_1$–$C_6$ alkyl groups;

$R^4$ represents a hydrogen atom, a $C_1$–$C_6$ alkyl group, a $C_2$–$C_6$ alkenyl group, a $C_2$–$C_6$ alkynyl group, an aryl group or an aromatic heterocyclic group, one of said aklyl, alkenyl or alkynyl groups being unsubstituted or having at least one substituent selected from the group consisting of:

$C_1$–$C_6$ alkoxy groups, trifluoromethyl groups and halogen atoms;

$R^5$ and $R^6$ are the same or different and each represents a hydrogen atom, a $C_1$–$C_6$ alkyl group, a $C_2$–$C_6$ alkenyl group or a $C_2$–$C_6$ alkynyl group;

X, Y and Z are the same or different and each represents a hydrogen atom, a $C_1$–$C_6$ alkyl group, a $C_1$–$C_6$ alkoxy group, a $C_1$–$C_6$ alkanoyloxy group, a hydroxy group, a $C_1$–$C_6$ alkylthio group, a cyano group, an amino group, a halogen atom, a $C_1$–$C_6$ alkylsulfinyl group, or a $C_1$–$C_6$ alkylsulfonyl group; and n is 0, 1 or 2;

said aryl groups are $C_6$–$C_{14}$ carbocyclic aryl groups which are unsubstituted or have at least one substituent selected from the group consisting of $C_1$–$C_6$ alkyl groups and substituents (a') other than said aryl groups; and said aromatic heterocyclic groups are selected from the group consisting of 2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl;

said aromatic heterocyclic groups being unsubstituted or having at least one substituent selected from the group consisting of $C_1$–$C_6$ alkyl groups and substituents (a') other than said heterocyclic groups;

provided that $R^2$, $R^4$, $R^5$ and $R^6$ are not all selected from the group consisting of hydrogen atoms and unsubstituted alkyl, alkenyl and alkynyl groups;

or a pharmaceutically acceptable ester, amide or salt thereof.

4. The compound as claimed in claim 1, wherein:
$R^1$, $R^4$ and $R^5$ all represent hydrogen atoms;
$R^2$ represents a $C_3$–$C_6$ cycloalkyl group, an aryl group, an aralkyl group, an aromatic heterocyclic group or a $C_1$–$C_3$ alkyl group having an aromatic heterocyclic substituent, said groups being unsubstituted or having at least one substituent selected from the group consisting of:
$C_1$–$C_4$ alkyl groups, $C_1$–$C_4$ alkoxy groups, $C_1$–$C_6$ alkanoyloxy groups, hydroxy groups, trifluoromethyl groups and halogen atoms;
$R^6$ represents a hydrogen atom, a $C_1$–$C_4$ alkyl group, a $C_2$–$C_4$ alkenyl group or a $C_2$–$C_4$ alkynyl group;
X, Y and Z are independently selected from the group consisting of hydrogen atoms, $C_1$–$C_4$ alkyl groups and halogen atoms; and
n is 0.

5. The compound as claimed in claim 1, wherein said ester is selected from the group consisting of $C_1$–$C_6$ alkyl esters, aralkyl esters, diarylalkyl esters, alkoxycarbonylmethyl esters where the alkoxy part is $C_1$–$C_4$, 2-(alkoxycarbonyloxy)ethyl esters where the alkoxy part is $C_1$–$C_4$, phthalidyl esters and (5-methyl-2-oxo-1,3-dioxolen-4-yl)methyl esters.

6. The compound of claim 1, which is 4-[1-Phenyl-2-(imidazol-1-yl)ethylthio]benzoic acid or a pharmaceutically acceptable salt thereof.

7. The compound of claim 1, which is 4-[1-(2,4-Dichlorophenyl)-2-(imidazol-1-yl)ethylthio]benzoic acid or a pharmaceutically acceptable salt thereof.

8. The compound of claim 1, which is 4-[1-(2-Chlorophenyl)-2-(imidazol-1-yl)ethylthio]benzoic acid or a pharmaceutically acceptable salt thereof.

9. The compound of claim 1, which is 4-[1-(2-Methylphenyl)-2-(imidazol-1-yl)ethylthio]benzoic acid or a pharmaceutically acceptable salt thereof.

10. The compound of claim 1, which is 4-[1-(2,4,6-Trimethylphenyl)-2-(imidazol-1-yl)ethylthio]benzoic acid or a pharmaceutically acceptable salt thereof.

11. The compound of claim 1, which is 4-[1-(2-Trifluoromethylphenyl)-2-(imidazol-1-yl)ethylthio]benzoic acid or a pharmaceutically acceptable salt thereof.

12. The compound of claim 1, which is 4-[1-(2-Methoxyphenyl)-2-(imidazol-1-yl)ethylthio]benzoic acid or a pharmaceutically acceptable salt thereof.

13. The compound of claim 1, which is 4-[1-(2,4-Dimethoxyphenyl)-2-(imidazol-1-yl)ethylthio]benzoic acid or a pharmaceutically acceptable salt thereof.

14. The compound of claim 1, which is 4-[1-(2,6-Dimethoxyphenyl)-2-(imidazol-1-yl)ethylthio]benzoic acid or a pharmaceutically acceptable salt thereof.

15. The compound of claim 1, which is 4-[1-(2,4,6-Trimethoxyphenyl)-2-(imidazol-1-yl)ethylthio]benzoic acid or a pharmaceutically acceptable salt thereof.

16. The compound of claim 1, which is 4-[1-(2-Hydroxyphenyl)-2-(imidazol-1-yl)ethylthio]benzoic acid or a pharmaceutically acceptable salt thereof.

17. The compound of claim 1, which is 4-[3-(4-Chlorophenyl)-1-(imidazol-1-ylmethyl)propylthio]benzoic acid or a pharmaceutically acceptable salt thereof.

18. The compound of claim 1, which is 4-[1-(2-Thienyl)-2-(imidazol-1-yl)ethylthio]benzoic acid or a pharmaceutically acceptable salt thereof.

19. The compound of claim 1, which is 4-[1-(2-Furyl)-2-(imidazol-1-yl)ethylthio]benzoic acid or a pharmaceutically acceptable salt thereof.

20. A compound as claimed in claim 4, wherein said ester is selected from the group consisting of $C_1$–$C_6$ alkyl esters, aralkyl esters, diarylalkyl esters, alkoxycarbonylmethyl esters where the alkoxy part is $C_1$–$C_4$, 2-(alkoxycarbonyloxy)ethyl esters where the alkoxy part is $C_1$–$C_4$, phthalidyl esters and (5-methyl-2-oxo-1,3-dioxolen-4-yl)methyl esters.

21. A composition useful to treat or prevent diseases and disorders arising from an imbalance in the level of $TXA_2$ comprising an effective amount of active compound to treat or prevent said diseases and disorders in admixture with a pharmaceutically acceptable carrier or diluent, wherein the active compound is selected from the group consisting of compounds of formula (I):

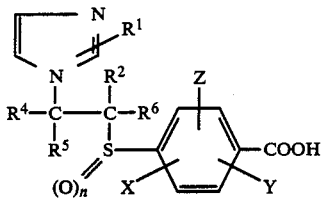

wherein:
$R^1$ represents a hydrogen atom or a methyl group;
$R^2$ represents a hydrogen atom, a $C_1$-$C_6$ alkyl group, a $C_2$-$C_6$ alkenyl group, a $C_2$-$C_6$ alkynyl group, a $C_3$-$C_8$ cycloalkyl group, a $C_3$-$C_8$ cycloalkyl group having at least one substituent selected from $C_1$-$C_6$ alkyl groups, an aryl group, a heterocyclic group or a carboxy group, or one of said alkyl, alkenyl and alkynyl groups having at least one substituent selected from the group consisting of:
(a) $C_1$-$C_4$ alkoxy groups, $C_1$-$C_6$ alkanoyloxy groups, $C_1$-$C_6$ alkanoyl groups, carboxy groups, $C_2$-$C_7$ alkoxycarbonyl groups, $C_2$-$C_7$ alkoxycarbonyloxy groups, carbamoyloxy groups, alkylcarbamoyloxy groups in which the alkyl part is $C_1$-$C_4$ alkyl, dialkylcarbamoyloxy groups in which each alkyl part is $C_1$-$C_4$ alkyl, carbamoyl groups, alkylcarbamoyl groups in which the alkyl part is $C_1$-$C_4$ alkyl, dialkylcarbamoyl groups in which each alkyl part is $C_1$-$C_4$ alkyl, hydroxy groups, carboxylic acylamino groups, $C_1$-$C_6$ alkylthio groups, nitro groups, cyano groups, amino groups, $C_1$-$C_6$ haloalkyl groups, halogen atoms, $C_1$-$C_6$ alkylsulfinyl groups, $C_1$-$C_6$ alkylsulfonyl groups, aryl groups, heterocyclic groups $C_3$-$C_8$ cycloalkyl groups, and $C_3$-$C_8$ cycloalkyl groups having at least one substituent selected from $C_1$-$C_6$ alkyl groups;
$R^4$ represents a hydrogen atom, a $C_1$-$C_6$ alkyl group, a $C_2$-$C_6$ alkenyl group, a $C_2$-$C_6$ alkynyl group, an aryl group or an aromatic heterocyclic group, or said alkyl, alkenyl or alkynyl group having at least one substituent selected from the group consisting of:
$C_1$-$C_6$ alkoxy groups, $C_1$-$C_6$ haloalkyl groups, halogen atoms, aryl groups and aromatic heterocyclic groups;
$R^5$ and $R^6$ are independently selected from the group consisting of hydrogen atoms, $C_1$-$C_6$ alkyl groups, $C_2$-$C_6$ alkenyl groups and $C_2$-$C_6$ alkynyl groups;
X, Y and Z are independently selected from the group consisting of hydrogen atoms, $C_1$-$C_6$ alkyl groups, $C_1$-$C_6$ alkoxy groups, $C_1$-$C_6$ alkanoyloxy groups, hydroxy groups, $C_1$-$C_6$ alkylthio groups, cyano groups, amino groups, halogen atoms, $C_1$-$C_6$ alkylsulfinyl groups and $C_1$-$C_6$ alkylsulfonyl groups;
n is 0, 1 or 2
said aryl groups are $C_6$-$C_{14}$ carbocyclic aryl groups which are unsubstituted or have at least one substituent selected from the group consisting of $C_1$-$C_6$ alkyl groups and substituents (a) other than said aryl groups; and
said aromatic heterocyclic groups are selected from the group consisting of
2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl;
said heterocyclic groups are selected from the group consisting of
2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl; and 2-tetrahydrofuryl, 2-tetrahydropyranyl, 2-pyrrolidinyl, 1-pyrrolidinyl, piperidino, 2-piperidyl, 3-piperidyl, 4-piperidyl, 4-thiazolidinyl, 1-piperazinyl, 4-acetyl-1-piperazinyl, 4-formyl-1-piperazinyl, morpholino and thiomorpholino;
said heterocyclic groups and said aromatic heterocyclic groups being unsubstituted or having at least one substituent selected from the group consisting of $C_1$-$C_6$ alkyl groups and substituents (a) other than said heterocyclic groups;
provided that when both $R^2$ and $R^6$ are individually selected from the group consisting of hydrogen and alkyl, then at least one of $R^4$ and $R^5$ is not selected from the group consisting of hydrogen, unsubstituted alkyl and unsubstituted alkenyl
or a pharmaceutically acceptable ester, amide or salt thereof.

22. The composition as claimed in claim 21, wherein $R^2$, $R^4$, $R^5$ and $R^6$ are as defined in claim 21, provided that they are not all selected from the group consisting of hydrogen atoms and unsubstituted alkyl, alkenyl and alkynyl groups.

23. A composition useful to treat or prevent diseases and disorders arising from an imbalance in the level of $TXA_2$ comprising an effective amount of active compound to treat or prevent said diseases and disorders in admixture with a pharmaceutically accpetable carrier or diluent, wherein the active compound is selected from the group consisting of compounds of formula (I):

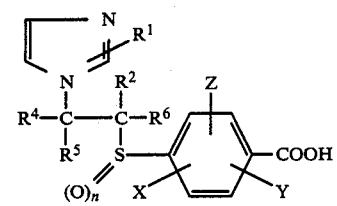

wherein:
$R^1$ represents a hydrogen atom or a methyl group;
$R^2$ represents a hydrogen atom, a $C_1$-$C_6$ alkyl group, a $C_2$-$C_6$ alkenyl group, a $C_2$-$C_6$ alkynyl group, a $C_3$-$C_6$ cycloalkyl group, an aryl group or an aromatic heterocyclic group, one of said alkyl, alkenyl or alkynyl groups being unsubstituted or having at least one substituent selected from the group consisting of substituents (a'):
(a') $C_1$-$C_6$ alkoxy groups, $C_1$-$C_6$ alkanoyloxy groups, hydroxy groups, $C_1$-$C_6$ alkylthio groups, cyano groups, trifluoromethyl groups, halogen atoms, $C_1$-$C_6$ alkylsulfinyl groups, $C_1$-$C_6$ alkylsulfonyl groups, aryl groups and aromatic heterocyclic groups,
or said cycloalkyl group having at least one substituent selected from $C_1$-$C_6$ alkyl groups;
$R^4$ represents a hydrogen atom, a $C_1$-$C_6$ alkyl group, a $C_2$-$C_6$ alkenyl group, a $C_2$-$C_6$ alkynyl group, an aryl group or an aromatic heterocyclic group, one of said aklyl, alkenyl or alkynyl groups being unsubstituted or having at least one substituent selected from the group consisting of:
$C_1$–$C_6$ alkoxy groups, trifluoromethyl groups and halogen atoms;
$R^5$ and $R^6$ are the same or different and each represents a hydrogen atom, a $C_1$–$C_6$ alkyl group, a $C_2$–$C_6$ alkenyl group or a $C_2$–$C_6$ alkynyl group;
X, Y and Z are the same or different and each represents a hydrogen atom, a $C_1$–$C_6$ alkyl group, a $C_1$–$C_6$ alkoxy group, a $C_1$–$C_6$ alkanoyloxy groups, a hydroxy group, a $C_1$–$C_6$ alkylthio group, a cyano group, an amino group, a halogen atom, a $C_1$–$C_6$ alkylsulfinyl group, or a $C_1$–$C_6$ alkylsulfonyl group; and
n is 0, 1 or 2;
said aryl groups are $C_6$–$C_{14}$ carbocyclic aryl groups which are unsubstituted or have at least one substituent selected from the group consisting of $C_1$–$C_6$ alkyl groups and substituents (a') other than said aryl groups; and
said aromatic heterocyclic groups are selected from the group consisting of
2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl;
said aromatic heterocyclic groups being unsubstituted or having at least one substituent selected from the group consisting of $C_1$–$C_6$ alkyl groups and substituents (a') other than said heterocyclic groups;
provided that $R^2$, $R^4$, $R^5$ and $R^6$ are not all selected from the group consisting of hydrogen atoms and unsubstituted alkyl, alkenyl and alkynyl groups;
or a pharmaceutically acceptable ester, amide or salt thereof.

24. The composition as claimed in claim 21, wherein:
$R^1$, $R^4$ and $R^5$ all represent hydrogen atoms;
$R^2$ represents a $C_3$–$C_6$ cycloalkyl group, an aryl group, an aralkyl group, an aromatic heterocyclic group or a $C_1$–$C_3$ alkyl group having an aromatic heterocyclic substituent, said groups being unsubstituted or having at least one substituent selected from the group consisting of:
$C_1$–$C_4$ alkyl groups, $C_1$–$C_4$ alkoxy groups, $C_1$–$C_6$ alkanoyloxy groups, hydroxy groups, trifluoromethyl groups and halogen atoms;
$R^6$ represents a hydrogen atom, a $C_1$–$C_4$ alkyl group, a $C_2$–$C_4$ alkenyl group or a $C_2$–$C_4$ alkynyl group;
X, Y and Z are independently selected from the group consisting of hydrogen atoms, $C_1$–$C_4$ alkyl groups and halogen atoms; and
n is 0.

25. The composition as claimed in claim 21, wherein said ester is selected from the group consisting of $C_1$–$C_6$ alkyl esters, aralkyl esters, diarylalkyl esters, alkoxycarbonylmethyl esters where the alkoxy part is $C_1$–$C_4$, 2-(alkoxycarbonyloxy)ethyl esters where the alkoxy part is $C_1$–$C_4$, phthalidyl esters and (5-methyl-2-oxo-1,3-dioxolen-4-yl)methyl esters.

26. The composition as claimed in claim 21, wherein said active compound is selected from the group consisting of:
4-[1-Phenyl-2-(imidazol-1-yl)ethylthio]benzoic acid;
4-[1-(2,4-Dichlorophenyl)-2-(imidazol-1-yl)ethylthio]benzoic acid;
4-[1-(2-Chlorophenyl)-2-(imidazol-1-yl)ethylthio]benzoic acid;
4-[1-(2-Methylphenyl)-2-(imidazol-1-yl)ethylthio]benzoic acid;
4-[1-(2,4,6-Trimethylphenyl)-2-(imidazol-1-yl)ethylthio]benzoic acid;
4-[1-(2-Trifluoromethylphenyl)-2-(imidazol-1-yl)ethylthio]benzoic acid;
4-[1-(2-Methoxyphenyl)-2-(imidazol-1-yl)ethylthio]benzoic acid;
4-[1-(2,4-Dimethoxyphenyl)-2-(imidazol-1-yl)ethylthio]benzoic acid;
4-[1-(2,6-Dimethoxyphenyl)-2-(imidazol-1-yl)ethylthio]benzoic acid;
4-[1-(2,4,6-Trimethoxyphenyl)-2-(imidazol-1-yl)ethylthio]benzoic acid;
4-[1-(2-Hydroxyphenyl)-2-(imidazol-1-yl)ethylthio]benzoic acid;
4-[3-(4-Chlorophenyl)-1-(imidazol-1-ylmethyl)propylthio]benzoic acid;
4-[1-(2-Thienyl)-2-(imidazol-1-yl)ethylthio]benzoic acid;
4-[1-(2-Furyl)-2-(imidazol-1-yl)ethylthio]benzoic acid;
or a pharmaceutically acceptable salt thereof.

27. A composition as claimed in claim 24, wherein said ester is selected from the group consisting of $C_1$–$C_6$ alkyl esters, aralkyl esters, diarylalkyl esters, alkoxycarbonylmethyl esters where the alkoxy part is $C_1$–$C_4$, 2-(alkoxycarbonyloxy)ethyl esters where the alkoxy part is $C_1$–$C_4$, phthalidyl esters and (5-methyl-2-oxo-1,3-dioxolen-4-yl)methyl esters.

28. A method for the treatment or prophylaxis of diseases and disorders arising from an imbalance in the level of $TXA_2$ in an animal, which comprises administering to said animal an effective amount of an inhibitor of the synthesis of $TXA_2$, wherein said inhibitor is selected from the group consisting of compounds of formula (I):

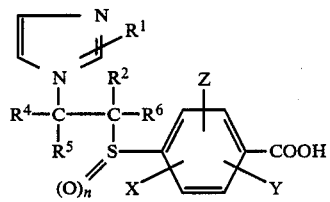

wherein:
$R^1$ represents a hydrogen atom or a methyl group;
$R^2$ represents a hydrogen atom, a $C_1$–$C_6$ alkyl group, a $C_2$–$C_6$ alkenyl group, a $C_2$–$C_6$ alkynyl group, a $C_3$–$C_8$ cycloalkyl group, a $C_3$–$C_8$ cycloalkyl group having at least one substituent selected from $C_1$–$C_6$ alkyl groups, an aryl group, a heterocyclic group or a carboxy group, or one of said alkyl, alkenyl and alkynyl groups having at least one substituent selected from the group consisting of:
(a) $C_1$–$C_4$ alkoxy groups, $C_1$–$C_6$ alkanoyloxy groups, $C_1$–$C_6$ alkanoyl groups, carboxy groups, $C_2$–$C_7$ alkoxycarbonyl groups, $C_2$–$C_7$ alkoxycarbonyloxy groups, carbamoyloxy groups, alkylcarbamoyloxy groups in which the alkyl part is $C_1$–$C_4$ alkyl, dialkylcarbamoyloxy groups in which each alkyl part is $C_1$–$C_4$ alkyl, carbamoyl groups, alkylcarbamoyl groups in which the alkyl part is $C_1$–$C_4$ alkyl, dialkylcarbamoyl groups in which each alkyl part is $C_1$–$C_4$ alkyl, hydroxy groups, carboxylic acylamino groups, $C_1$–$C_6$ alkylthio groups, nitro groups, cyano groups, amino groups, $C_1$–$C_6$ haloalkyl groups, halogen atoms, $C_1$–$C_6$ alkylsulfinyl groups, $C_1$–$C_6$ alkylsulfonyl groups, aryl groups, heterocyclic groups $C_3$–$C_8$ cycloalkyl groups, and $C_3$–$C_8$ cycloalkyl groups having at least one substituent selected from $C_1$–$C_6$ alkyl groups;

$R^4$ represents a hydrogen atom, a $C_1$–$C_6$ alkyl group, a $C_2$–$C_6$ alkenyl group, a $C_2$–$C_6$ alkynyl group, an aryl group or an aromatic heterocyclic group, or said alkyl, alkenyl or alkynyl group having at least one substituent selected from the group consisting of:
  $C_1$–$C_6$ alkoxy groups, $C_1$–$C_6$ haloalkyl groups, halogen atoms, aryl groups and aromatic heterocyclic groups;

$R^5$ and $R^6$ are independently selected from the group consisting of hydrogen atoms, $C_1$–$C_6$ alkyl groups, $C_2$–$C_6$ alkenyl groups and $C_2$–$C_6$ alkynyl groups;

X, Y and Z are independently selected from the group consisting of hydrogen atoms, $C_1$–$C_6$ alkyl groups, $C_1$–$C_6$ alkoxy groups, $C_1$–$C_6$ alkanoyloxy groups, hydroxy groups, $C_1$–$C_6$ alkylthio groups, cyano groups, amino groups, halogen atoms, $C_1$–$C_6$ alkylsulfinyl groups and $C_1$–$C_6$ alkylsulfonyl groups;

n is 0, 1 or 2 said aryl groups are $C_6$–$C_{14}$ carbocyclic aryl groups which are unsubstituted or have at least one substituent selected from the group consisting of $C_1$–$C_6$ alkyl groups and substituents (a) other than said aryl groups; and said aromatic heterocyclic groups are selected from the group consisting of
  2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl;

said heterocyclic groups are selected from the group consisting of
  2-furyl, 3-furyl, 2-thienyl, 3-thienyl, 2-thiazoyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl; and 2-tetrahydrofuryl, 2-tetrahydropyranyl, 2-pyrrolidinyl, 1-pyrrolidinyl, piperidino, 2-piperidiyl, 3-piperidyl, 4-piperidyl, 4-thiazolidinyl, 1-piperazinyl, 4-acetyl-1-piperazinyl, 4-formyl-1-piperazinyl, morpholino and thiomorpholino;

said heterocyclic groups and said aromatic heterocyclic groups being unsubstituted or having at least one substituent selected from the group consisting of $C_1$–$C_6$ alkyl groups and substituents (a) other than said heterocyclic groups;

provided that when both $R^2$ and $R^6$ are individually selected from the group consisting of hydrogen and alkyl, then at least one of $R^4$ and $R^5$ is not selected from the group consisting of hydrogen, unsubstituted alkyl and unsubstituted alkenyl;

or a pharmaceutically acceptable ester, amide or salt thereof.

29. The method as claimed in claim 28, wherein $R^2$, $R^4$, $R^5$ and $R^6$ are as defined in claim 28, provided that they are not all selected from the group consisting of hydrogen atoms and unsubstituted alkyl, alkenyl and alkynyl groups.

30. A method for the treatment or prophylaxis of diseases and disorders arising from an imbalance in the level of $TXA_2$ in an animal, which comprises administering to said animal an effective amount of an inhibitor of the synthesis of $TXA_2$, wherein said inhibitor is selected from the group consisting of compounds of formula (I):

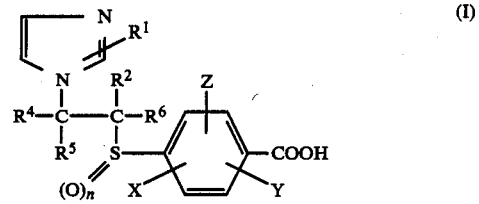

wherein:
  $R^1$ represents a hydrogen atom or a methyl group;
  $R^2$ represents a hydrogen atom, a $C_1$–$C_6$ alkyl group, a $C_2$–$C_6$ alkenyl group, a $C_2$–$C_6$ alkynyl group, a $C_3$–$C_6$ cycloalkyl group, an aryl group or an aromatic heterocyclic group, one of said alkyl, alkenyl or alkynyl groups being unsubstituted or having at least one substituent selected from the group consisting of substituents (a'):
    (a') $C_1$–$C_6$ alkoxy groups, $C_1$–$C_6$ alkanoyloxy groups, hydroxy groups, $C_1$–$C_6$ alkylthio groups, cyano groups, trifluoromethyl groups, halogen atoms, $C_1$–$C_6$ alkylsulfinyl groups, $C_1$–$C_6$ alkylsulfonyl groups, aryl groups and aromatic heterocyclic groups,
  or said cycloalkyl group having at least one substituent selected from $C_1$–$C_6$ alkyl groups;
  $R^4$ represents a hydrogen atom, a $C_1$–$C_6$ alkyl group, a $C_2$–$C_6$ alkenyl group, a $C_2$–$C_6$ alkynyl group, an aryl group or an aromatic heterocyclic group, one of said aklyl, alkenyl or alkynyl groups being unsubstituted or having at least one substituent selected from the group consisting of:
    $C_1$–$C_6$ alkoxy groups, trifluoromethyl groups and halogen atoms;
  $R^5$ and $R^6$ are the same or different and each represents a hydrogen atom, a $C_1$–$C_6$ alkyl group, a $C_2$–$C_6$ alkenyl group or a $C_2$–$C_6$ alkynyl group;
  X, Y and Z are the same or different and each represents a hydrogen atom, a $C_1$–$C_6$ alkyl group, a $C_1$–$C_6$ alkoxy group, a $C_1$–$C_6$ alkanoyloxy group, a hydroxy group, a $C_1$–$C_6$ alkylthio group, a cyano group, an amino group, a halogen atom, a $C_1$–$C_6$ alkylsulfinyl group, or a $C_1$–$C_6$ alkylsulfonyl group; and
  n is 0, 1 or 2;
  said aryl groups are $C_6$–$C_{14}$ carbocyclic aryl groups which are unsubstituted or have at least one substituent selected from the group consisting of $C_1$–$C_6$ alkyl groups and substituents (a') other than said aryl groups; and
  said aromatic heterocyclic groups are selected from the group consisting of
    2-furyl, 3-furyl, 2-thienyl, 3-thienyl, 2-thiazolyl, 4-thiazolyl, 2-pyridyl, 3-pyridyl, 4-pyridyl, 2-pyrazinyl, 2-pyrrolyl, 1-methyl-2-pyrrolyl, 1-imidazolyl, 1,2,4-triazol-1-yl and 2-pyrimidyl;
  said aromatic heterocyclic groups being unsubstituted or having at least one substituent selected from the group consisting of $C_1$–$C_6$ alkyl groups and substituents (a') other than said heterocyclic groups;

provided that $R^2$, $R^4$, $R^5$ and $R^6$ are not all selected from the group consisting of hydrogen atoms and unsubstituted alkyl, alkenyl and alkynyl groups;

or a pharmaceutically acceptable ester, amide or salt thereof.

31. The method as claimed in claim 28, wherein:

$R^1$, $R^4$ and $R^5$ all represent hydrogen atoms;

$R^2$ represents a $C_3$-$C_6$ cycloalkyl group, an aryl group, an aralkyl group, an aromatic heterocyclic group or a $C_1$-$C_3$ alkyl group having an aromatic heterocyclic substituent, said groups being unsubstituted or having at least one substituent selected from the group consisting of:

$C_1$-$C_4$ alkyl groups, $C_1$-$C_4$ alkoxy groups, $C_1$-$C_6$ alkanoyloxy groups, hydroxy groups, trifluoromethyl groups and halogen atoms;

$R^6$ represents a hydrogen atom, a $C_1$-$C_4$ alkyl group, a $C_2$-$C_4$ alkenyl group or a $C_2$-$C_4$ alkynyl group;

X, Y and Z are independently selected from the group consisting of hydrogen atoms, $C_1$-$C_4$ alkyl groups and halogen atoms; and n is 0.

32. The method as claimed in claim 28, wherein said ester is selected from the group consisting of $C_1$-$C_6$ alkyl esters, aralkyl esters, diarylalkyl esters, alkoxycarbonylmethyl esters where the alkoxy part is $C_1$-$C_4$, 2-(alkoxycarbonyloxy)ethyl esters where the alkoxy part is $C_1$-$C_4$, phthalidyl esters and (5-methyl-2-oxo-1,3-dioxolen-4-yl)methyl esters.

33. The method as claimed in claim 28, wherein said inhibitor is selected from the group consisting of:

4-[1-Phenyl-2-(imidazol-1-yl)ethylthio]benzoic acid;

4-[1-(2,4-Dichlorophenyl)-2-(imidazol-1-yl)ethylthio]benzoic acid;

4-[1-(2-Chlorophenyl)-2-(imidazol-1-yl)ethylthio]benzoic acid;

4-[1-(2-Methylphenyl)-2-(imidazol-1-yl)ethylthio]benzoic acid;

4-[1-(2,4,6-Trimethylphenyl)-2-(imidazol-1-yl)ethylthio]benzoic acid;

4-[1-(2-Trifluoromethylphenyl)-2-(imidazol-1-yl)ethylthio]benzoic acid;

4-[1-(2-Methoxyphenyl)-2-(imidazol-1-yl)ethylthio]benzoic acid;

4-[1-(2,4-Dimethoxyphenyl)-2-(imidazol-1-yl)ethylthio]benzoic acid;

4-[1-(2,6-Dimethoxyphenyl)-2-(imidazol-1-yl)ethylthio]benzoic acid;

4-[1-(2,4,6-Trimethoxyphenyl)-2-(imidazol-1-yl)ethylthio]benzoic acid;

4-[1-(2-Hydroxyphenyl)-2-(imidazol-1-yl)ethylthio]benzoic acid;

4-[3-(4-Chlorophenyl)-1-(imidazol-1-ylmethyl)propylthio]benzoic acid;

4-[1-(2-Thienyl)-2-(imidazol-1-yl)ethylthio]benzoic acid;

4-[1-(2-Furyl)-2-(imidazol-1-yl)ethylthio]benzoic acid;

or a pharmaceutically acceptable salt thereof.

34. A method as claimed in claim 31, wherein said ester is selected from the group consisting of $C_1$-$C_6$ alkyl esters, aralkyl esters, diarylalkyl esters, alkoxycarbonylmethyl esters where the alkoxy part is $C_1$-$C_4$, 2-(alkoxycarbonyloxy)ethyl esters where the alkoxy part is $C_1$-$C_4$, phthalidyl esters and (5-methyl-2-oxo-1,3-dioxolen-4-yl)methyl esters.

* * * * *

UNITED STATES PATENT AND TRADEMARK OFFICE
CERTIFICATE OF CORRECTION

PATENT NO. : 4,894,385

DATED : January 16, 1990

INVENTOR(S) : KAWAMOTO et al

It is certified that error appears in the above-identified patent and that said Letters Patent is hereby corrected as shown below:

Column 4, line 36, change "an" to --and--.

Column 5, lines 35-36, change:

"2-(62-naphthyl-)ethyl groups" to

--2-($\beta$-naphthyl)ethyl groups--.

Column 26, line 13, change "J'8.0 Hz)" to

--J=8.0Hz)--.

Column 43. claim 23, line 12, change "groups" to

--group--.

Signed and Sealed this

Twenty-third Day of June, 1992

*Attest:*

DOUGLAS B. COMER

*Attesting Officer*    *Acting Commissioner of Patents and Trademarks*